United States Patent
Lundberg et al.

(10) Patent No.: US 10,406,118 B2
(45) Date of Patent: *Sep. 10, 2019

(54) USE OF NITRITES AND NITRATES AND COMPOSITIONS CONTAINING THESE

(76) Inventors: Jon Lundberg, Djursholm (SE); Eddie Weitzberg, Stockholm (SE)

(*) Notice: Subject to any disclaimer, the term of this patent is extended or adjusted under 35 U.S.C. 154(b) by 25 days.

This patent is subject to a terminal disclaimer.

(21) Appl. No.: 12/528,794

(22) PCT Filed: Feb. 26, 2008

(86) PCT No.: PCT/SE2008/050212
§ 371 (c)(1),
(2), (4) Date: Aug. 26, 2009

(87) PCT Pub. No.: WO2008/105731
PCT Pub. Date: Sep. 4, 2008

(65) Prior Publication Data
US 2010/0092441 A1    Apr. 15, 2010

Related U.S. Application Data

(60) Provisional application No. 60/919,709, filed on Mar. 22, 2007.

(30) Foreign Application Priority Data

Feb. 26, 2007 (SE) .................................. 0700520

(51) Int. Cl.
| | | |
|---|---|---|
| A23L 33/16 | (2016.01) |
| A61K 31/05 | (2006.01) |
| A61K 33/00 | (2006.01) |
| A61K 31/21 | (2006.01) |
| A61K 36/21 | (2006.01) |
| A61K 36/28 | (2006.01) |
| A61K 36/185 | (2006.01) |

(52) U.S. Cl.
CPC .............. A61K 31/05 (2013.01); A23L 33/16 (2016.08); A61K 31/21 (2013.01); A61K 33/00 (2013.01); A61K 36/185 (2013.01); A61K 36/21 (2013.01); A61K 36/28 (2013.01)

(58) Field of Classification Search
CPC ........ A61K 31/05; A61K 33/00; A61K 36/28; A61K 31/21; A61K 36/21; A61K 36/185; A23L 33/16
See application file for complete search history.

(56) References Cited

U.S. PATENT DOCUMENTS

| | | | |
|---|---|---|---|
| 4,702,922 A * | 10/1987 | Wiesenberger | A23L 2/02 426/51 |
| 4,868,179 A | 9/1989 | Cohn | |
| 6,024,992 A * | 2/2000 | Yoo | A23L 27/24 426/49 |
| 6,117,872 A | 9/2000 | Maxwell et al. | |
| 2004/0204371 A1 | 10/2004 | Cohn et al. | |
| 2005/0266018 A1 | 12/2005 | Boreyko et al. | |
| 2006/0182815 A1 | 8/2006 | Gladwin et al. | |
| 2010/0047344 A1 | 2/2010 | Lundberg et al. | |

FOREIGN PATENT DOCUMENTS

| | | |
|---|---|---|
| EP | 511587 A1 | 11/1992 |
| EP | 2008661 A2 | 12/2008 |
| KR | 200210057695 A | 7/2002 |
| WO | 2004/056376 A1 | 7/2004 |
| WO | 2005/04884 A2 | 1/2005 |
| WO | 2006/110601 A2 | 10/2006 |
| WO | 2007/014334 A2 | 2/2007 |

OTHER PUBLICATIONS

Osada K, Hoshina S, Nakamura S, Sugano M. Cholesterol oxidation in meat products and its regulation by supplementation of sodium nitrite and apple polyphenol before processing. J Agric Food Chem. 2000; 48: 3823-9.*
Hunter et al.., Nature Medicine, vol. 10, Oct. 2004, pp. 1122-1127.*
Xu et al., Applied Microbiology and Biotechnology, vol. 56, No. 3-4, Aug. 2001, pp. 504-507.*
De Vries et al., "Lactobacillus plantarum-survival, functional and potential probiotic properties in the human intestinal tract", International Dairy Journal, vol. 16, No. 9, Sep. 2006, pp. 1018-1028.*
Kirk et al. (Ann. Emerg. Med., Sep. 1993;22 :1 413-1418.)).*
Deng et al., Alcohol 34 (2004) 217-223.*
Classen et al., Journal of the American College of Nutrition, vol. 9. No. 5. 500-502 ( 1990).*
Gladwin et al., Nature Chemical Biology, vol. 1 No. 6 Nov. 2005, pp. 308-314.*
Bryan, Free Radical Biology & Medicine 41 (2006) 691-701.*
Grudzinski et al., Arch Environ Contam Toxicol. Sep. 1991;21(3):468-74.*
Grudzinski et al., Arch Environ Contam Toxicol. Sep. 1991;21(3):462-467.*
Yoon et al., Bioresource Technology 97 (2006) 1427-1430.*
Balzer, J. et al. (2007). "Reductase activity of polyphenols?: A commentary on 'Red wine-dependent reduction of nitrite to nitric oxide in the stomach'," *Free Radical Biology and Medicine* 43:1226-1228.

(Continued)

*Primary Examiner* — Kade Ariani
(74) *Attorney, Agent, or Firm* — Booth Udall Fuller PLC

(57) ABSTRACT

Inorganic anions nitrate and nitrite influence metabolic rate and glucose homeostasis. Infusion of nitrite iv caused an acute drop in resting energy expenditure (oxygen consumption) and nitrate, when given perorally, caused a drop in oxygen consumption during exercise and a depression of the increase in blood glucose observed after an oral glucose tolerance test. The doses of nitrate and nitrite did not cause any detectable change in methemoglobin levels of blood. Also, nitrate and nitrite did not alter lactate levels in blood. This discovery provides useful treatments to regulate the energy expenditure and glucose homeostasis of a mammal by administration of inorganic nitrite and/or nitrate.

18 Claims, 13 Drawing Sheets

(56) References Cited

OTHER PUBLICATIONS

Davidson, S. M. and Duchen, M. R. (2006). "Effects of NO on mitochondrial function in cardiomyocytes: Pathophysiological relevance," *Cardiovascular Research* 71:10-21.

Deng, X.-S. et al. (2004). "Formation of ethyl nitrite in vivo after ethanol administration," *Alcohol* 34:217-223.

Gago, B. et al. (2007). "Red wine-dependent reduction of nitrite to nitric oxide in the stomach," *Free Radical Biology and Medicine* 43:1233-1242.

Giulivi, C. et al. (2006). "Nitric oxide reduction of mitochondrial oxygen consumption I: cellular physiology," *American Journal of Physiology—Cell Physiology* 291:225-1231.

Grossi, L. and Strazzi, S. (1999). "A New Synthesis of Alkyl Nitrites: The Reaction of Alkyl Alcohols with Nitric Oxide in Organic Solvents," *Journal of Organic Chemistry* 64:8076-8079.

International Search Report dated Jun. 12, 2008, for PCT Application No. PCT/SE2008/050212 filed on Feb. 26, 2008, 9 pages.

International Written Opinion dated Jun. 12, 2008, for PCT Application No. PCT/SE2008/050212 filed on Feb. 26, 2008, 14 pages.

Lundberg, J. O. and Govoni, M. (2004). "Inorganic nitrate is a possible source for systemic generation of nitric oxide," *Free Radical Biology and Medicine* 37(3):395.

Peri, L. et al. (2005). "Apples increase nitric oxide production by human saliva at the acidic pH of the stomach: A new biological function for polyphenols with a catechol group?," *Free Radical Biology and Medicine* 39:668.

Shibata, M. et al. (Jul. 22, 2005). "Nitric oxide modulates oxygen consumption by arteriolar walls in rat skeletal muscle," *American Journal of Physiology: Heart Circulation Physiology* 289:H2673-H2679.

Shiva, S. et al. (2007). "Deoxymyoglobin is a Nitrite Reductase That Generates Nitric Oxide and Regulates Mitochondrial Respiration," *Circulation Research* 100:654-661.

Stamler et al, Science, 258:18981902 (1992).

Jungersten et al, J. Appl. Physiol., 82(3):760-764 (1997).

Iijima et al, Gastroenterology, 122:1248-1257 (2002).

Van Velzen et al, Toxicology Letters, 181:177-181 (2008).

Ferrannini, Metabolism, 37(3):287-301 (1988).

Hamel et al, Critical Care Nurse, 31(1):72-82 (2011).

Official Action from Corresponding European Application No. 08 712 840.1 dated Feb. 27, 2014.

Cohn, et al., A Comparison of Enalapril with Hydralazine-Isosorbide Dinitrate in the Treatment of Chronic Congestive Heart Failure, The New England Journal of Medicine, 325:303-310 (1991).

Tubau et al, Cardiovascular Research, 21:606-614 (1987).

Guazzi et al, The American Journal of Cardiology, 84:1038-1043 (1999).

Tian et al, Hypertension Research, 34:1221-1227 (2011).

Friberg et al, Journal of Hypertension, 4(2):165-173 (1986), Abstract only.

Shen et al, Circulation Research, 75(6):1086-1095 (1994).

McKnight et al, Gut, 40:211-214 (1997).

Bohuslavs'kyi, Fiziol Zh, 51(1):33-42 (2005), Abstract only.

Third Party Observations, filed Apr. 28, 2015 in EP 08712839.3.

Third Party Observations, filed Apr. 10, 2015 in EP 08712839.3.

Third Party Observations, filed Jul. 28, 2015 in EP 08712839.3.

\* cited by examiner

USE OF NITRITES AND NITRATES AND COMPOSITIONS CONTAINING THESE

CROSS REFERENCE TO RELATED APPLICATIONS

This is a U.S. National Phase patent application of PCT/SE2008/050212, filed Feb. 26, 2008, which claims priority to Swedish patent application Serial No. 0700520-0, filed Feb. 26, 2007, and U.S. Provisional patent application Ser. No. 60/919,709, filed Mar. 22, 2007, all of which are hereby incorporated by reference in the present disclosure in their entirety.

TECHNICAL FIELD

This invention relates to the field of medicine and pharmaceuticals, in particular pharmaceuticals and therapeutic methods for lowering metabolic rate, oxygen consumption and/or glucose homeostasis in a human patient or another mammal, based on the administration of nitrates and/or nitrites to said patient or mammal.

BACKGROUND ART

Nitrate ($NO_3^-$) and nitrite ($NO_2^-$) are generally viewed as unwanted residues in the food chain with potentially harmful effects (Joint FAO/WHOExpert Committee on Food Additives (JECFA). Safety Evaluation of Certain Food Additives. WHO, 1970. ISBN 9241660503; TANNENBAUM, S. R., et al. Nitrite in human saliva. Its possible relationship to nitrosamine formation. J cancer Ins. 1974, vol. 53, p. 79-84; BARTSCH, H., et al. Inhibitors of endogenous nitrosation: mechanisms and implications in human cancer prevention. Mutation Res. 1988, vol. 202, p. 307-324). Proposed harmful effects of these anions include promotion of gastric cancers and other malignancies and development of methemoglobinemia in infants. Because of this the levels of nitrate/nitrite are strictly regulated in food and drinking water.

Recent studies indicate that nitrate and nitrite can have significant biological effects in the body and that these effects may be beneficial (LUNDBERG, Jon O., et al. Nitrate, bacteria and human health. Nat Rev Microbiol. 2004, no. 2, p. 593-602). For example the nitrite anion can cause vasodilatation at near physiological concentrations when tested in vitro (MODIN, A., et al. Nitrite-derived nitric oxide: a possible mediator of 'acidic-metabolic' vasodilation. Acta Physiol Scand. 2001, vol. 171, p. 9-16) or when infused intra-arterially to humans (COSBY, K., et al. Nitrite reduction to nitric oxide by deoxyhemoglobin vasodilates the human circulation. Nat Med. 2003, no. 9, p. 1498-505). Nitrate can be converted to nitrite in vivo in a process dependent on commensal bacteria (SPIEGELHALDER, B., et al. Influence of dietary nitrate on nitrite content of human saliva: possible relevance to in vivo formation of N-nitroso compounds. Food Cosmet Toxicol. 1976, no. 14, p. 545-548). When nitrate is ingested it is rapidly absorbed into blood and then accumulates in saliva. In the oral cavity bacteria reduce parts of the dietary nitrate to nitrite and nitrite can then enter the systemic circulation. (LUNDBERG, Jon O., et al. Inorganic nitrate is a possible source for systemic generation of nitric oxide. Free Radic Biol Med. 2004, vol. 37, p. 395-400).

To date the focus among researchers has been on the cardiovascular effects of nitrite after its in vivo reduction to the vasodilator nitric oxide (NO) (COSBY et al. (supra); DURANSKI, M. R., et al. Cytoprotective effects of nitrite during in vivo ischemia-reperfusion of the heart and liver. J Clin Invest. 2005, vol. 115, p. 1232-1240; GLADWIN, M. T., et al. The emerging biology of the nitrite anion. Nat Chem Biol. 2005, no. 1, p. 308-14; LARSEN, F. J., et al. Effects of dietary nitrate on blood pressure in healthy volunteers. N Engl J Med. 2006, vol. 355, p. 2792-3).

WO 2005/004884 A (US GOVERNMENT ET AL.) 2005 Jan. 20 and WO 2005/007173 A (US GOVERNMENT ET AL.) 2005 Jan. 27 describe a method to administer a nitrite salt specifically to obtain vasodilatation in a subject. No effects of low-dose nitrate/nitrite on energy expenditure or glucose homeostasis have been described.

SUMMARY OF THE INVENTION

The inventors have surprisingly shown that the metabolic rate and/or the oxygen consumption can be influenced in a mammal (locally in isolated tissues or organs or systemically in the whole body), by administering inorganic nitrite ($NO_2^-$) and/or nitrate ($NO_3^-$) to said mammal in an amount of nitrite and/or nitrate sufficient to decrease oxygen consumption. The oxygen consumption is decreased without causing significant hypotension and does not cause any significant increase of the methemoglobin level in said mammal.

The invention also makes available a method for lowering the metabolic rate in a mammal, wherein a pharmaceutical composition comprising inorganic nitrite ($NO_2^-$) and nitrate ($NO_3^-$) is administered to said mammal in an amount of nitrite and nitrate which is sufficient to decrease oxygen consumption. The oxygen consumption is decreased without causing significant hypotension.

In particular, the invention makes available a method for lowering the metabolic rate in a mammal, wherein a pharmaceutical composition comprising inorganic nitrite ($NO_2^-$) is administered to said mammal in an amount of nitrite which is sufficient to decrease oxygen consumption. The oxygen consumption is decreased without causing significant hypotension. The nitrite can be administered perorally or parenterally. When administered parenterally, said nitrite can be administered intravenously at a dose of about 0.01 to about 10 000 nmoles/kg/min.

The invention also makes available a method for lowering the metabolic rate in a mammal, wherein a pharmaceutical composition comprising inorganic nitrate ($NO_3^-$) is administered to said mammal in an amount of nitrate which is sufficient to decrease oxygen consumption, but which does not increase methemoglobin levels in said mammal, wherein said nitrate is administered perorally in the form of a nitrate salt at a dose of about 0.01 to about 100 mmol/kg/24 h. When given perorally, nitrate can be seen as a precursor of nitrite.

The invention also makes available a composition, use and method wherein inorganic nitrite and/or nitrate is/are combined with polyphenols.

The influence on, or regulation of, metabolic rate and/or oxygen consumption can be used as a step in the treatment, prevention or amelioration of a pathological or physiological condition where metabolic stress is a distinctive feature. Such stress may be present in e.g. intensive care patients, patients undergoing surgery, patients with malnutrition, patients with cancer and anorexia, patients with burn injury, trauma patients, neonates and prematures, patients with anorexia nervosa, patients scheduled for solid organ transplantation or patients having undergone an solid organ transplantation. In addition, a decrease in oxygen consumption with a lower need for oxygen in the tissues, is desirable in any pathological situation characterized by low oxygen availability, including; chronic obstructive pulmonary disease (COPD), inflammatory airway disease such as asthma, pulmonary hypertension, congestive heart disease, interstitial lung disease, pulmonary embolism, ischemic heart disease, peripheral artery disease; sleep apnea syndrome.

The inventive findings can also be applied to the regulation of the metabolic rate as a step in treating, preventing or ameliorating a condition of disturbed glucose homeostasis (glucose control) including: diabetes mellitus type 1 and type 2, prediabetes, intensive care patients, surgical trauma, metabolic syndrome, obesity, burn injury, drug-induced diabetes. The term "glucose control" is used in its broadest sense, as it is known that the stabilization of blood glucose levels is important for many reasons and concerns many patient groups, as well as healthy subjects. It is general knowledge that diabetic patients are susceptible to complications such as neuropathies, cardiomyopathy, vascular disease, poor wound healing and blindness. Even patients suffering with simple hypoglycaemia would benefit from glucose control. Further it is hypothesised that many common health conditions other than diabetes have a component of insufficient or disturbed glucose control. For example obesitas is closely associated with glucose and insulin. It is also suggested that emotional problems such as concentration difficulties and mood swings are associated with poor glucose control. Due to the well documented adverse effects of hyperglycaemia as well as hypoglycemia, it is important to maintain proper glucose control in both diabetic and non-diabetic patients/subjects.

The invention also provides methods for treatment, alleviation and/or prevention of clinical conditions, comprising administering an effective amount of a nitrate and/or a nitrite to a patient in need thereof sufficient to treat, alleviate and/or prevent such condition.

As a consequence of the present findings and the conclusions reached by the inventors, the present invention also makes available new uses of nitrites and/or nitrates, for the manufacture of pharmaceutical products, enteral or parenteral nutritional solutions, or nutritional supplements, for administration to both healthy persons, such as athletes, or to patients, suffering from one or more of the conditions exemplified in the description.

Further embodiments will become evident to the skilled person upon study of the figures, description and examples, as well as the appended claims, incorporated herein by reference.

BRIEF DESCRIPTION OF THE DRAWINGS

The invention will be described in closer detail in the following description, non-limiting examples and claims, with reference to the attached drawings in which:

DETAILED DESCRIPTION OF THE INVENTION

Definitions

Figure 1:
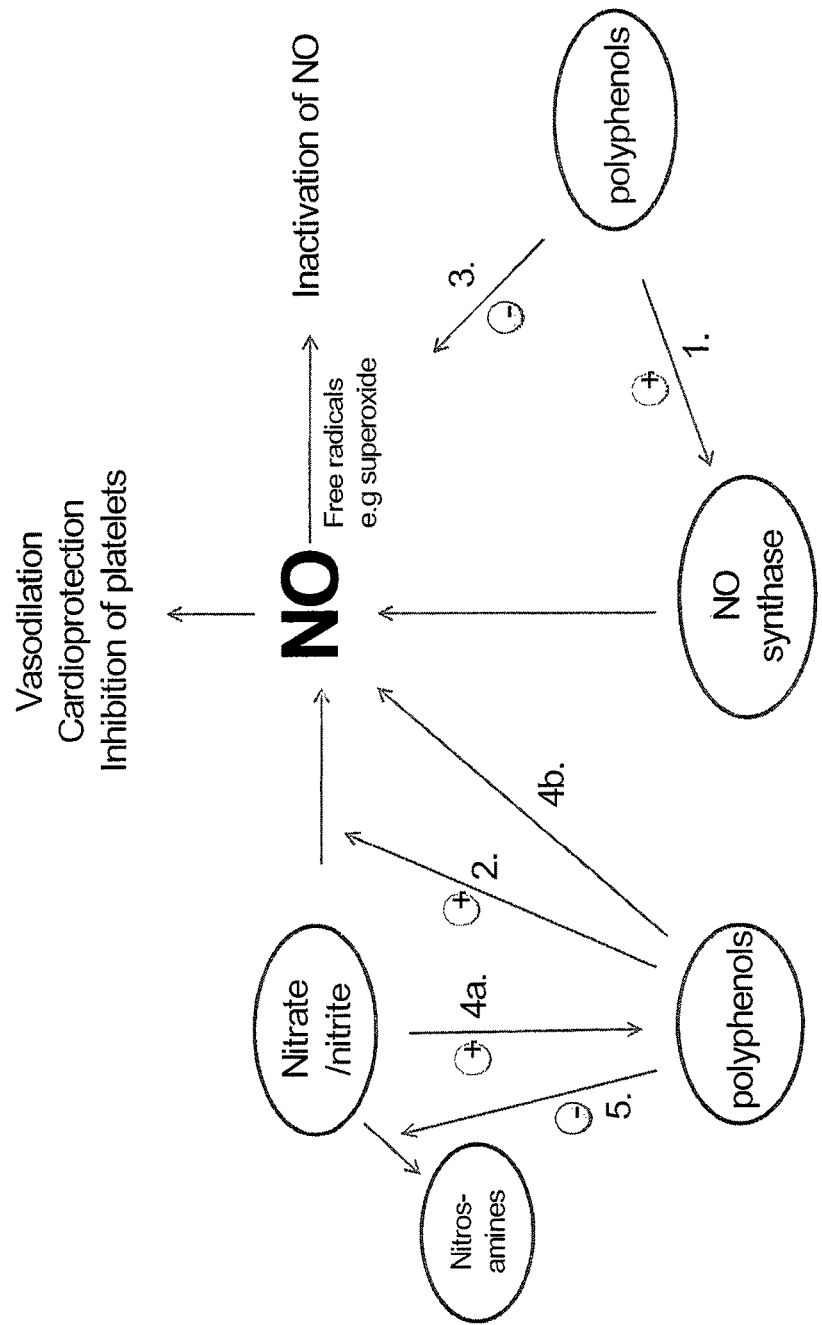
FIG. 1 shows a graph illustrating numerous ways in which the combination of nitrate and polyphenols synergistically act to increase the bioavailability of nitric oxide and at the same time to reduce the formation of harmful compounds such as oxygen radicals and nitrosamines. For detailed explanation see text.

Before the present method and compositions are described in the form of embodiments thereof, it is to be understood that this invention is not limited to the particular configurations, method steps, and materials disclosed herein as such configurations, steps and materials may vary somewhat. It is also to be understood that the terminology employed herein is used for the purpose of describing particular embodiments only and is not intended to be limiting since the scope of the present invention will be limited only by the appended claims and equivalents thereof.

It must also be noted that, as used in this specification and the appended claims, the singular forms "a", "an", and "the" include plural referents unless the context clearly dictates otherwise.

The term "about" when used in the context of numeric values denotes an interval of accuracy, familiar and acceptable to a person skilled in the art. Said interval can be +/−2% of the given value, preferably +/−5%, and most preferably +/−10% of the numeric values, where applicable.

The term "mammal" is intended to encompass all mammals, and in particular humans, pets and agriculturally significant animals, as well as animals used in competitions, such as horses and dogs.

The term "significant hypotension" means in this context an acute reduction of systolic and/or diastolic blood pressure, accompanied by clinical symptoms of hypotension such as dizziness, nausea, pallor, loss of consciousness, etc. Said symptoms may occur in various degrees, and it is preferred that they are entirely avoided, minimized or eliminated as far as possible, or at least to an extent that they are clinically insignificant.

The term "metabolic syndrome" is here defined as a combination of medical disorders that increase the risk for cardiovascular disease and diabetes in a human. Symptoms and feature include fasting hyperglycaemia, diabetes mellitus type 2 or impaired fasting glucose, impaired glucose tolerance or insulin resistance, high blood pressure, central obesity, decreased HDL cholesterol, elevated triglycerides and elevated uric acid levels.

The term "insulin resistance" is here defined as a condition in which normal amounts of insulin are inadequate to produce a normal insulin response from fat, muscle and liver cells.

The term "metabolism" is used to define the complete set of chemical reactions that occur in living cells and "metabolic rate" is defined as the speed of metabolism of a mammal. The term "energy expenditure" is here defined as the amount of energy expended for a certain metabolic rate.

The term "oxygen consumption" is defined as the amount of oxygen ($O_2$) consumed by a mammal and is usually expressed as ml of pure oxygen consumed/min. "Oxygen consumption" relates to the amount of oxygen consumed by a mammal as whole but also to oxygen consumption in an isolated tissue or organ, such as, but not limited to, heart, liver brain or other tissue exposed to ischemia.

Methemoglobin is a form of hemoglobin in which the iron in the heme group is in the $Fe^{3+}$ state, not the $Fe^{2+}$ of normal hemoglobin. Methemoglobin is unable to carry oxygen. Methemoglobinemia is defined as a blood disorder characterized by the presence of a higher than normal level of methemoglobin in the blood.

The term "catabolism" is defined as the metabolic process that breaks down molecules into smaller units. It is made up of degradative chemical reactions in the living cell.

The term "functional food" relates to any fresh or processed food claimed to have a health-promoting and/or disease-preventing property beyond the basic nutritional function of supplying nutrients. Functional foods are sometimes called nutraceuticals. The general category includes processed food made from functional food ingredients, or fortified with health-promoting additives, like "vitamin-enriched" products, and also, fresh foods (eg vegetables) that have specific claims attached. Fermented foods with live cultures are often also considered to be functional foods with probiotic benefits.

The inventors have surprisingly shown that the metabolic rate and/or the oxygen consumption can be influenced in a mammal (locally or systemically), by administering inorganic nitrite ($NO_2$-) and/or nitrate ($NO_3$-) to said mammal in an amount of nitrite and/or nitrate sufficient to decrease oxygen consumption. The decreased oxygen consumption is achieved without causing significant hypotension and without causing any significant increase of the methemoglobin level in said mammal. In case of local reduction of the metabolic rate, the oxygen consumption is decreased in an isolated tissue or organ such as the heart, liver, brain or other tissue that is exposed to ischemia (a condition in which blood flow, and thus oxygen, is restricted to a part of the body). In such cases the interaction of reaction products (including NO) of nitrite and/or nitrate with enzymes of the mitochondrial respiratory chain and subsequent inhibition of respiration leads to lowering of oxygen demand which is beneficial for an ischemic tissue. This effect resembles hibernation. Because the generation of active nitrite and/or nitrate reaction products are maximized in ischemic tissues the effect of oxygen consumption will be most pronounced at these sites. In one particular embodiment, the oxygen consumption is lowered in the heart.

The surprising finding that nitrite and its precursor nitrate affects such vital physiological processes as metabolic rate and/or oxygen consumption can be used therapeutically, e.g. in prophylaxis, alleviation or treatment of several conditions. In an attempt to increase systemic nitrite levels, nitrite and/or nitrate can be given by enteral administration (orally, in the form of a liquid, semi-solid or solid preparation, such as a chewing gum, tablet, lozenge, wafer, cake, bar or the like) or by parenteral administration (intravenous, transdermal, transcutaneous, by inhalation, rectally, vaginally, topical, intraperitoneally, intra muscular, subcutaneous, sublingual or any other way of parenteral administration). The nitrite and/or nitrate comprising composition and possible further combinations described herein can be administered continuously or as single bolus doses.

In principle, also other additional approaches can lead to increased systemic or local nitrite levels. The most obvious is to administer nitrite or its precursor nitrate as such, but this may be supplemented by or enhanced by increasing the gastric pH (e.g. with an acid suppressive drug such as a proton pump inhibitor or $H_2$ receptor antagonist or antacida) to maximise nitrite survival in the stomach and thereby the systemic delivery of nitrite. Alternatively, the administration of nitrite or nitrate can be supplemented by or enhanced by interfering with the oral microflora in order to maximise the number of nitrate reducing species. This can be achieved through the delivery of "probiotic" nitrate reducing bacteria or selective treatment with an antibiotic to favour the nitrate reducing species.

It is likely that an optimal dose-interval exists, meaning that below a certain plasma level of nitrite the effects are insufficient and correspondingly, that over a certain level the effect is lower, and possibly accompanied by side effects. Using intravenous administration, the nitrite is preferably administered in a dose within the interval of about 0.01 to about 10,000 nmoles/kg/min, preferably about 0.01 to about 1000 nmoles/kg/min, more preferably about 0.1 to about 100 nmoles/kg/min, most preferably about 1 to about 20 nmoles/kg/min. It is presently contemplated that the most preferred dose is less than about 15 nmoles/kg/min. For comparison, it should be noted that the nitrite dose used in the treatment of cyanide poisoning is about 100 000 nmoles/kg, or about 300-400 mg given as a single dose. The nitrite can also be administered as one or more bolus doses, preferably 0.01-

100 µmoles/kg body weight, more preferably 0.1-10 µmoles/kg body weight, and even more preferably 0.1-2 µmoles/kg body weight.

For the use of a nitrate salt perorally, a dose of about 0.01-100 mmol/kg/24 h is currently preferred or more preferably a dose of about 0.01-10 mmol/kg/24 h, even more preferably 0.1-1 mmol/kg/24 h.

Importantly, the administered dose of nitrate or nitrite should not induce production of more than about 10% methemoglobin, preferably not more than about 5% methemoglobin, and more preferably not more than about 2% methemoglobin. Most preferred is that the dose of nitrate or nitrite does not induce any measurable change in methemoglobin in the subject when administered or ingested according to the prescribed dose.

Combinations of nitrate and nitrite salts can also be used. According to one embodiment, nitrate and nitrite are given orally in a dose ratio interval of about 5:1 to about 100:1 (nitrate:nitrite), such as 5:1, 10:1, 30:1, 50:1, 70:1 and 100:1. Preferably the dose ratio is about 10:1. This will ensure acute effects of the nitrite as soon as it is absorbed, and then provide a sustained effect of the nitrate following its bioconversion into nitrite.

In one embodiment the composition comprising inorganic nitrite and/or nitrate is a pharmaceutical composition comprising inorganic nitrite and/or nitrate in an amount which is sufficient to decrease oxygen consumption, but which does not increase the methemoglobin level in a subject when administered to said subject in a prescribed dose. Optionally the composition comprises another pharmaceutically active compound.

Alternatively, the composition comprising nitrite and/or nitrate is a nutritional supplement, an enteral nutritional solution, an infant formula, a snack product or a parenteral nutritional solution comprising inorganic nitrite and/or nitrate in an amount which is sufficient to decrease oxygen consumption, but which does not cause significant hypotension in a subject when ingested by said subject in a prescribed dose.

Pharmaceutically acceptable salts of nitrate and nitrite include but are not limited to sodium, potassium, calcium, zinc, arginine and ammonium. Sodium and potassium salts are presently most preferred. The nitrite and nitrate salts may be of synthetic origin, but may also be isolated from natural sources, such as naturally nitrate containing plants, e.g. green leafy vegetables, examples include, but are not limited to spinach, lettuce, fennel, cabbage, Chinese cabbage and beetroot. Concentrates, such as juices or dried concentrates of these and other nitrate-rich vegetables or fruits are suitably used for the manufacture of food products (including functional food products) or nutritional supplements according to the present invention.

Polyphenols are a group of chemical substances found in plants, characterized by the presence of more than one phenol group per molecule. Polyphenols are generally further subdivided into hydrolyzable tannins, which are gallic acid esters of glucose and other sugars; and phenylpropanoids, such as lignins, flavonoids, and condensed tannins. In one embodiment of the present invention the inorganic nitrite and/or nitrate is/are mixed with a compound that contains high levels of polyphenols. It is contemplated that this combination will have synergistic health promoting effects via potentiation of NO bioavailability. Polyphenols will enhance NO generation by several separate mechanisms highlighted in FIG. 1. First, such agents can directly stimulate endogenous NO formation from NO synthase enzymes (1 in FIG. 1). Second, it is contemplated that these compounds will enhance the reduction of nitrite to bioactive NO due to the presence of reductive —OH groups on the phenol ring (2 in FIG. 1). Third, by acting as scavengers of free radicals such as superoxide, they prevent these radicals from interacting with (and destroying) NO and thereby, NO becomes more long-lived (3 in FIG. 1). In addition to this, nitrite or its reaction products can interact with the polyphenol itself and modify it chemically via nitration or nitrosation reactions (4a in FIG. 1). The resulting compound can act as a long-lived NO donor (4b in FIG. 1). An additional effect is that the presence of polyphenols will divert the chemical reactions away from formation of potentially carcinogenic nitrosamines (5 in FIG. 1). Nitrates reaction product nitrite can react with amines to form nitrosamines but polyphenols will inhibit this reaction by a dual mechanism. First they help to rapidly reduce $HNO_2$ directly to NO thereby minimizing the formation of nitrosating species ($N_2O_3$, $HNO_2$). Second, they can directly compete for nitrosation with the amines by being nitrosated themselves.

In one embodiment of the present invention inorganic nitrite and/or nitrate is administered or used in combination with a polyphenol rich compound or product. The ratio nitrite/nitrate comprising composition:polyphenol-rich compound should be chosen to obtain enough supply of nitrate. The nitrite/nitrate comprising composition should therefore be at least about 10%, preferably at least about 20%, more preferably at least about 30%, even more preferably at least about 40% and most preferably at least about 50% or even more. It is contemplated that the combination of nitrite/nitrate and polyphenol rich compound or product will act synergistically to enhance NO formation in the body at the expense of detrimental compounds such as nitrosamines. The beneficial effects of this includes a reduction in blood pressure and platelet aggregation, reduced atherosclerosis, reduced risk of myocardial infarction, stroke and other cardiovascular disorders, reduced risk of cancer in any form. Examples of polyphenol rich fruit or juices thereof include, but are not limited to, apple, pear, grapes, lemon, orange, lime, peach, pomegranate, grapefruit, kiwi, ginger and pineapple. Juice from berries are also usable including blackberries, black raspberries, blueberries, cranberries, red raspberries, cherries, bog wortleberry, lingonberries, black elderberry, black chokeberry, black currant, blueberry, cloudberries and strawberries. Other natural sources of polyphenols include vegetables such as carrots, chili, rhubarb, onions. In addition, cacao products (rich in flavanols), green or black tea, nuts, Yerba mate and coffee are all rich in polyphenols. In one preferred embodiment the nitrate in the inventive composition originates from beetroot (such as beetroot juice) which is blended with one or several polyphenol-rich compounds or products. The ratio beetroot juice:polyphenol-rich compound should be chosen to obtain enough supply of nitrate and therefore the beetroot juice part should be at least about 10%, preferably at least about 20%, more preferably at least about 30%, even more preferably at least about 40% and most preferably at least about 50%.

According to one embodiment of the present invention the dose of nitrite and/or nitrate or nitrite and/or nitrate together with polyphenols is administered or manufactured as a chewing gum, lozenge or pastille, wafer, cake, bar or the like which optionally also comprises live non-pathogenic bacteria. It can also be administered or manufactured as a functional food product or as a part of a functional food product.

The use of nitrite and/or nitrate or a combination of nitrate and/or nitrite with polyphenols may also have beneficial effects on the blood pressure. Thus, in one embodiment the present invention relates to a method to reduce blood pressure, preferably to normal levels (about 140/80 mmHg). Examples of nitrite and/or nitrate sources are natural sources of nitrate (such as vegetables as mentioned above or juices thereof) or salts of nitrite and/or nitrate. In one particular embodiment beetroot or a juice thereof is administered in order to reduce the blood pressure in a mammal.

The purpose with the combination with non-pathogenic live bacteria is to further enhance the generation of bioactive compounds such as NO, nitroso adducts or chemically related compounds. This enhancement will occur locally in the GI tract via bacteria-dependent reduction of nitrate and nitrite to NO and other bioactive nitrogen oxides. In particular, this combination will be effective in treating and preventing GI disorders such as ulcers in the stomach, duodenum, jejunum, caecum and colon/rectum. Also, it is contemplated that this combined product will be effective in treating and preventing inflammatory bowel disorders including ulcerative colitis, Crohn's disease, microscopic colitis and other forms. Irritable bowel disease (IBS) is another condition that could be treated with said product. In addition, the compounds formed can be absorbed systemically and have sustained biological effects for example in reducing blood pressure and in preventing atherosclerosis, cancer or any other effect related to enhance NO release as discussed above. Suitable bacteria are the so called probiotic bacteria, included but not limited to *Lactobacilli* (for example *L. acidophilus, L. delbrueckii, L. helveticus, L. salivarius, L. casei, L. curvatus, L. plantarum, L. sakei, L. brevis, L. buchneri, L. fermentum, L. reuteri*) and *Bifidobacteria* species such as *B. breve, B. bifidum*, and *B. lactis* and probiotic yeasts such a *Saccharomyces boulardii*. Other suitable non-pathogenic bacteria that enhance nitrate reduction or nitrite reduction include e.g. *Veillonella* species, *Staphylococcus* species, *Actinomyces* species or *Rothia* species. These microorganisms may also be included in "dry form" for example in tablets, capsules, bars, and alike.

In one embodiment a low concentration of ethanol is added to the inorganic nitrite and/or nitrate composition. In one embodiment ethanol is used in combination with or administered together with the inorganic nitrite and/or nitrate composition. It has surprisingly been found that ethanol even in very low concentrations can generate the potent vasodilator ethyl nitrite following reaction with physiological amounts of nitrite. The reaction is enhanced at acidic conditions such as in the gastric lumen. It is contemplated that ingestion of nitrate will lead to accumulation of nitrite in the saliva and the nitrite will react with ethanol in the stomach thereby forming ethyl nitrite. For example, if the inventive composition is in the form of a liquid the ethanol content should be below about 5% (v/v), more preferably below about 2% (v/v), and most preferable between about 0.5-1.5% (v/v).

In one embodiment of the present invention a cacao product such as dark chocolate that is rich in flavanols is combined with a nitrate-rich natural compound in a drink or a chocolate bar. One preferred nitrate-rich compound in this embodiment is rhubarb. Again, the nitrate will potentiate the effect of the flavanols via enhancement of NO formation as described above and in FIG. 1.

Contamination of a nitrate-containing food or drink with unwanted bacteria may result in a large accumulation of nitrite, due to nitrate reducing bacterial enzymes. Ingestion of high levels of nitrite may cause potentially serious methemoglobinemia. In one embodiment a nitrate-rich composition is mixed with a compound that inhibits unwanted bacterial growth. Such compound should be chosen so as not to affect the taste of the product negatively. Ideally, it should enhance the taste and at the same time increase the bioactivity of the product. One option is to acidify the inventive composition so that final pH is below about 5, and most preferably between about pH 2-4. This will inhibit and/or abolish bacterial growth. Suitable acidifying agents can be any agent that reduces pH and include artificial compounds as well as natural juices from e.g, but not limited to, lemon or lime, ascorbic acid, acetic acid or vinegar (from apple, grapes or other fruits). It is contemplated that with the use of natural products a dual effect is achieved. Besides having an antibacterial effect, they are rich in polyphenols, which enhance the generation of bioactive NO from nitrate/nitrite in the vegetable drink. In one particular embodiment a nitrate-rich vegetable juice (e.g. beetroot juice) is mixed with a compound that inhibits undesirable bacterial growth.

According to an embodiment of the invention, the nitrate and nitrite salts are combined with other pharmaceuticals including but not limited to: anti-diabetic drugs (insulin and oral anti-diabetics), cardiovascular drugs (statins, ACE inhibitors, beta-receptor antagonists, diuretics, angiotensin 2 receptor antagonists, organic nitrates, calcium channel blockers) acid secretion-inhibitors (proton pump inhibitors, Histamine-2 receptor blockers), oral anti-diabetics including biguanides, sulphonureides, alpha-glucosidase inhibitors, thiazolidinediones, glinides; drugs for treatment of pulmonary hypertension including prostacyclin analogues, endothelin receptor antagonists and sildenafil.

According to one embodiment the nitrite is delivered systemically via peroral treatment with an organic nitrate including nitroglycerine or isosorbide mono/di-nitrate. Nitroglycerine is used clinically to treat angina pectoris and it acts by releasing vasodilatory nitric oxide systemically. However, this drug must be given parenterally because the first passage metabolism in the liver is considerable. Interestingly, it has been found that the liver metabolism of nitroglycerine yields predominantly nitrite. Considering the novel biological effects of nitrite described here, nitroglycerine may therefore be used as a "prodrug" of nitrite. Preferably the drug should then be given by the enteral route (with liver metabolism) to maximize nitrite generation while at the same time avoiding the acute vasodilatation and drop in systemic blood pressure associated with iv or sublingual administration of nitroglycerine. A suitable dose range when giving nitroglycerine perorally is about 0.001 to 10 mol/kg/24 hours, preferably about 0.001 to 1 mol/kg/24 hours, more preferably 0.01 to about 0.1 mmol/kg/24 hours. The tablets should preferably be coated to avoid absorption in the oral cavity.

According to one embodiment nitrite and/or nitrate is added to parenteral and enteral feeding/nutrition solutions to be used in adults, children, neonates and prematures. Today such solutions are generally extremely low in nitrate and nitrite as noted in measurements performed by the present inventors (not shown). An intubated mechanically ventilated patient with parenteral nutrition is particularly deprived of nitrate/nitrite. First, these patients do not produce and swallow saliva properly and thus one great nitrate/nitrite source is disrupted. Secondly as stated above, the feeding they receive contains almost no nitrate/nitrite. Many intensive care patients suffer from metabolic disturbances, in particular catabolism due to stress and trauma and their metabolic rate is often increased. Moreover, insulin resistance is common and glucose homeostasis is disturbed. Tight control of plasma glucose by administering insulin is advocated in these patients. Also healthy subjects, such as infants or subjects taking enteral solutions for other reasons can benefit from the compositions and methods of the present invention. Enteral nutrition is thus meant to include also infant formulas and other enteral products.

In one embodiment, provided herein are uses of nitrites and/or nitrates, for the manufacture of pharmaceutical products, enteral or parenteral nutritional solutions, preoperative compositions, nutritional supplements, or functional food products for administration to both healthy persons, such as athletes, or to patients, suffering from one or more of the conditions exemplified herein. Included in this embodiment are also possible combinations of nitrites and/or nitrates with other compounds as mentioned above.

In one embodiment, provided herein are methods for the treatment, alleviation and/or prevention of clinical conditions, comprising administering an effective amount of a nitrate and/or a nitrite to a patient in need thereof sufficient to treat, alleviate and/or prevent such condition.

There are many possible clinical conditions where such treatment, alleviation and/or prevention is performed using nitrate and/or nitrite according to the present invention:
  glucose control in diabetes/prediabetes
  metabolic syndrome The method and composition according to the invention also has general therapeutic, alleviating and/or prophylactic effects in patients under metabolic stress. Examples include but are not limited to:
  intensive care patients
  patients undergoing surgery
  patients suffering from malnutrition of different genesis
  cancer with anorexia
  burn injury
  trauma
  neonates/prematures
  anorexia nervosa
  thyreoidea disorders (e.g. hyperthyreosis)
  myocardial infarction, cardiac arrest
  major systemic disease with a catabolic state
  stress ulcers (gastric)
  surgical gut anastomosis insufficiency
  fever
  myocardial infarction and cardiac arrest
  ischemia-reperfusion injury (MI, stroke, arterial insufficiency or any other organ ischemia)
  sleep apnoea syndrome
  septic chock
  insufficient perfusion of the intestines Patients treated in the ICU (intensive care unit) are often subjected to severe metabolic stress due to trauma, infection, pain and other pathological processes. Such patients are treated for several reasons including but not limited to post surgical observation, trauma, bleeding, burn injury, brain injury, stroke, diabetes, sepsis, septic shock, myocardial infarction, cardiac arrest, arterial insufficiency or any other organ ischemia, chronic obstructive pulmonary disease, asthma and other severe inflammatory conditions, pulmonary hypertension, congestive heart failure, pulmonary embolism. This results in varying degrees of catabolism and resistance to insulin with a disturbed glucose handling. They also often suffer from vascular endothelial dysfunction leading to microcirculatory disturbances. As mentioned above these patients are given only minute amounts of nitrate/nitrite in the enteral and parenteral feeding and due to several reasons (sedation, intubation) they have a disturbed enterosalivary circulation of nitrate/nitrite compared to healthy people.

It is contemplated that addition of sufficient amounts of nitrite and/or nitrate in the parenteral and/or enteral feeding to patients treated in the intensive care unit, may alleviate or prevent the aforementioned metabolic and circulatory disturbances by decreasing the rate of metabolism, enhancing blood glucose homeostasis and microcirculatory improvement.

Patients undergoing surgery are subjected to a varying degree of surgical trauma. This triggers catabolic hormones like cortisol, glucagon and adrenalin and such patients may develop transient insulin resistance. Common clinical procedure involves fasting in order to reduce gastric content which could be accidentally aspirated in the airways if the patient vomits or regurgitates during anaesthesia. Such fasting eliminates the intake of nitrate/nitrite and it has been shown that systemic levels of nitrate and nitrite are reduced after fasting. It is contemplated that administration of nitrite and/or nitrate pre, per or postoperatively will improve the metabolic situation (decreasing the rate of metabolism, enhancing blood glucose homeostasis) in surgical patients. Moreover, during the entire perioperative period the patients are at higher risk for ischemic events due to hypotension, hypoxia and microcirculatory disturbances. Such events will initiate ischemia-reperfusion processes which may injure several organ systems within the body. It is contemplated that prophylactic administration of nitrite and/or nitrate, either as a preoperative drink containing nitrate and/or nitrite anions, a suitable vegetable juice such as but not limited to beetroot juice or by giving nitrate and/or nitrite via the parenteral route, will reduce the negative effects of ischemia-reperfusion events during surgery in several organs including but not limited to brain, heart, lung, liver, kidney and skeletal muscle.

Ischemia-reperfusion injury during myocardial infarction is a major problem in clinical care. State-of-the art treatment of myocardial infarction includes reopening of occluded coronary vessels by pharmacological means with thrombolytic agents and/or percutaneous coronary intervention. It is considered that the method and composition according to the invention will reduce ischemia-reperfusion injury by increasing blood flow and by altering mitochondrial function. From experiments in the present application it is also considered that during ischemia-reperfusion nitrate and nitrite could reduce oxygen consumption possibly by a "hibernating" effect on mitochondria. Another mechanism by which nitrate and nitrite could ameliorate ischemia-reperfusion injury is by reducing oxygen radical formation and cytochrome C release from the mitochondria. The effect of nitrate and nitrite on mitochondrial function is most likely mediated by nitric oxide (NO) interacting with oxidative phosphorylation and/or s-nitrosylation of protein complexes in the mitochondrial respiratory chain. It is envisaged that the time point for administration of nitrate and/or nitrite in relation to the myocardial infarction induced ischemia-reperfusion injury will be effective both pre, per or post injury. Both a pre and post conditioning effect of nitrate and/or nitrite is considered which means that a patient can receive treatment already in the ambulance on his/her way to the hospital, at the hospital before and after reperfusion of the coronary circulation and also at the ward. Also patients at high risk of developing a myocardial infarction (eg. angina pectoris, congestive heart failure) could be considered for prophylactic treatment with the method and composition according to the invention. After cardiac arrest and resuscitation systemic ischemia-reperfusion injury develops involving several major organ systems, including the brain. It is contemplated that nitrate and/or nitrite is beneficial both given prophylactic to patients with high risk for cardiac arrest and also during resuscitation procedures.

According to a preferred embodiment, the nitrate and/or nitrite or any combination mentioned herein is/are also given pre-operatively to patients scheduled to undergo surgery or substantive, invasive examination procedures. In one particular embodiment, inorganic nitrite and/or nitrate are combined with carbohydrates. Thus, such combinations include, but are not limited to nitrate alone; nitrate and nitrite; nitrate, nitrite, and carbohydrates; nitrate and carbohydrates; nitrite alone and nitrite and carbohydrates. In addition polyphenols may be added to any of the aforementioned combinations. Any such combination can be administered (in single or repeated doses) as a preoperative drink or the like prior to surgery or intravenously prior or during surgery. An appropriate time to administer such a preoperative drink is between 72 and 2 hours before surgery. A combination of nitrite and/or nitrate with carbohydrates may ameliorate insulin resistance and also ischemia/reperfusion injury common in the preoperative and postoperative period. Examples of carbohydrates include but are not limited to glucose, fructose, maltodextrin, sucrose, lactose, galactose and mannose. When given preoperatively the amount of carbohydrates in the drink will provide the patient with preferably about 200 kcal, more preferably about 100 kcal and most preferably about 50 kcal. For the use of a nitrate salt perorally, a dose of about 0.01-100 mmol/kg/24 h is currently preferred or more preferably a dose of about 0.01-10 mmol/kg/24 h, even more preferably 0.1-1 mmol/kg/24 h.

Using intravenous administration pre and/or peroperatively, the nitrite is preferably administered in a dose within the interval of about 0.01 to about 10 000 nmoles/kg/min, preferably about 0.01 to about 1000 nmoles/kg/min, more preferably about 0.1 to about 100 nmoles/kg/min, most preferably about 1 to about 20 nmoles/kg/min. It is presently contemplated that the most preferred dose is less than about 15 nmoles/kg/min In patients suffering from arterial insufficiency, including but not limited to intermittent claudication, pharmacological treatment aims at improving blood flow in the affected limb(s) and to stimulate angiogenesis to promote new vessel formation. Phosphodiesterase inhibitors and growth factors have been studied in clinical trials but results are variable. Likewise, studies with traditional NO donors such as organic nitrates have been less successful. It is contemplated that the method and composition according to the invention will positively stimulate both blood flow and angiogenesis thereby improving the condition in these patients. Treatment with nitrate/nitrite is attractive since it will preferentially increase blood flow in the ischemic areas without causing troublesome systemic effects such as hypotension which is a risk when using organic nitrates that dilate non-selectively in most vascular beds. In addition, nitrite will affect mitochondrial function as discussed above resulting in less oxygen demand in the ischemic tissue.

In patients suffering from malnutrition, including but no limited to cancer with anorexia, anorexia nervosa, gastrointestinal disease, it is contemplated that the method and composition according to the invention will have an anabolic effect and will reduce oxygen consumption. It is contemplated that this effect is achieved by improving mitochondrial efficiency and attenuating mitochondrial uncoupling.

The method and composition according to the invention also has general therapeutic effects in patients with erectile dysfunction. In this condition the endogenous NO system is failing. Administration of nitrite and/or nitrate (and possible combinations outlined above) will enhance NO formation locally in the corpus cavernosum, thereby enhancing erection.

It is contemplated that the method and composition according to the invention has general therapeutic, alleviating and/or prophylactic effects in patients with gastritis and gastric ulcers due to *Helicobacter pylori* infection, stress or side-effects from pharmacological treatment such as the use of Non-Steroidal Anti-Inflammatory Drugs (NSAID). By improving gastric mucosal blood flow, mucus generation and by anti-bacterial and antiinflammatory properties the method and composition will have beneficial effects in these patients. In addition unwanted side-effects of treatment with acetylsalicylic acid, NSAIDs or any other ulcerogenic drug in other parts of the gastrointestinal tract (duodenum, small and large intestines) are prevented by said method and composition.

A feared problem in surgery is gut anastomosis insufficiency and insufficient perfusion of the intestines. New methods for improving microcirculation in the anastomosis are constantly investigated. It is contemplated that the method and composition according to the invention will improve microcirculation in the anastomosis which will enhance the healing process. It is also considered that the invention will improve circulation in situations with insufficient perfusion of the intestines.

Patients with sleep apnoea syndrome are at higher risk for developing hypertension and other cardiovascular diseases. Moreover, they are subjected to periods of hypoxia during sleep. It is contemplated that the method and composition according to the invention will protect against hypoxia-induced injury by improving circulation and by reducing oxygen consumption possibly by a "hibernating" effect on mitochondria. Other mechanism by which said method and composition could have protective effects is by reducing oxygen radical formation and cytochrome C release from the mitochondria. The effect of nitrate and nitrite on mitochondrial function is most likely mediated by nitric oxide (NO) interacting with oxidative phosphorylation and/or s-nitrosylation of complexes in the mitochondrial respiratory chain.

The method and composition according to the invention has general therapeutic, alleviating and/or prophylactic effects also in patients with pathological conditions characterized by low oxygen availability, including but not limited to chronic obstructive airway disease (COPD), inflammatory airway disease such as asthma, pulmonary hypertension, congestive heart disease, interstitial lung disease, pulmonary embolism, ischemic heart disease, peripheral artery disease, sleep apnéa syndrome, myocardial infarction and systemic inflammatory disorders. In these conditions addition of oxygen promptly improve arterial oxygenation and total body oxygen delivery. For technical and safety reasons it is complicated to administer oxygen outside hospital facilities. Another way to improve the situation for these patients is to reduce the need for oxygen. The method and composition according to the invention lead to reduced oxygen cost in relation to the physical work performed. This highly surprising finding is especially relevant in the patients with the aforementioned conditions since oxygen availability is the limiting factor for physical activity. It is envisaged that the method and composition according to the invention will facilitate physical activity in these patients groups.

In one preferred embodiment nitrate and/or nitrite is given to patients with a pathological condition characterized by low oxygen availability. In such situations it is desirable to reduce the tissues need for oxygen to prevent sequele and symptoms associated with the hypoxia. Examples include patients with COPD whose pulmonary oxygen uptake may be severely compromised and patients with peripheral artery disease where oxygen delivery to the tissues is reduced.

The inventive method and composition is also useful for healthy subjects, e.g. athletes. The inventive method and composition provides for less oxygen demand at a certain workload and improves anabolism. The method and composition is also useful for oxygen sparing at high altitude, for example in work and sports performed in a low oxygen environment, such as but not limited to rescue activities, fire fighting, military operations, diving, mountain climbing, high-altitude flying, and the exploration of space.

The present method and composition is also useful in solid organ or tissue transplantation, in order to minimize metabolic demand of the donated organ before transplantation, and to improve survival of the transplanted organ or tissue after transplantation. Nitrite and/or nitrate or any combination mentioned herein is/are given either into the organ or tissue by perfusion, topically on the organ or tissue and/or systemically to the donor before transplantation, and into the organ or tissue by perfusion or topically on the organ or tissue and/or systemically to the receiver after transplantation.

In one preferred embodiment nitrate and/or nitrite is/are or any combination mentioned herein given to patients that are at risk of developing significant metabolic stress. Such situations include many of the conditions listed above including surgical stress and trauma. Oxygen demand and consumption increases dramatically during stress. Thus, an improved situation is achieved by decreasing the oxygen demand in these patients. According to one preferred embodiment nitrate and/or nitrite is given to patients to prevent the sequele associated with physiologic or traumatic stress. Examples include patients that come into the emergency room after trauma or patients undergoing major surgery.

To the best of the knowledge of the inventors, this is the first study to examine the effects of dietary nitrate on the cardiopulmonary and metabolic response to exercise. The main finding was that dietary supplementation with inorganic nitrate, in an amount which does not cause significant hypotension and without any significant increase in methemoglobin and plasma lactate, results in a reduced $VO_2$ during submaximal work and a significant increase in muscular efficiency. These effects occurred without any changes in $VO_{2peak}$ values or maximal attainable work rate.

Without wishing to be bound by theory, the inventors consider that there is reason to believe that the observed effects involve initial reduction of nitrate to nitrite. Nitrate itself is believed to be biologically inert and cannot be metabolised by mammalian cells. However, after ingestion nitrate re-enters into the mouth via the salivary glands and is effectively reduced by commensal bacteria thereby forming nitrite. In contrast to nitrate the nitrite ion has recently been shown to possess a wide range of bioactivities. In the present study the inventors did indeed note an increase in plasma nitrite after the nitrate treatment period thereby confirming in vivo reduction of nitrate as described previously. Another finding in support of nitrite being bioactive was its effective consumption during exercise in contrast to the unchanged levels of plasma nitrate. Ultimately the bioactivity of nitrite is likely related to its further reduction to NO and possibly other closely related nitrogen intermediates. In addition, it has been recently suggested that, nitrite itself may directly affect cellular signaling pathways. Although probably unlikely, at this stage effects of the nitrate ion itself cannot be excluded. There are several principle ways by which biological effects of nitrogen oxides may be propagated including activation of cGMP, alteration of protein function by a nitro(syl)ation/nitration or direct binding to protein heme-moieties of several proteins as in the prototypic activation of guanylyl cyclase by NO. In addition, nitrite itself may also directly affect cellular signaling pathways.

If the effects proceed via nitrate reduction to nitrite and then NO formation, how could this then explain the present results? Earlier studies using NOS inhibitors to block endogenous NO production give some indications. NOS-inhibition has been shown to increase submaximal $VO_2$ in dogs during exercise, independently of the reduction in blood flow. This increase in $VO_2$ during NOS-blockade has been linked to the fact that NO affects tissue respiration in vitro by reversible inhibition of the respiratory enzyme cytochrome c oxidase. Others have related the increased $VO_2$ during NOS-blockade to an inhibiting effect of NO on proton leakage via the mitochondrial permeability transition pore (mPTP) were a considerable amount of protons leak over the inner mitochondrial membrane. If the effects of nitrate were solely due to inhibition of cytochrome c oxidase (thereby inhibiting oxidative phosphorylation) one would expect an increase in anaerobic metabolism during physical exercise and a larger accumulation of lactate. However, judging from the results this was not the case, as the plasma lactate concentration was near identical after nitrate supplementation compared to placebo.

The finding that the oxygen pulse at a given work rate decreases by nitrate supplementation is a direct effect of the lower oxygen demand at that work rate. However, there is no difference in oxygen pulse at a given absolute oxygen uptake. The lack of effect of nitrate on $VE/VO_2$ or oxygen pulse indicates that the improved efficiency originates from muscular or mitochondrial adaptations rather than from central adaptations in the heart or the lungs.

EXAMPLES

The present inventors have been studying the effects of nitrate and nitrite on various physiological functions including blood pressure, glucose metabolism and energy expenditure in vivo. In the examples below nitrate was administered perorally and nitrite was administered intravenously (iv). Oxygen consumption was measured using indirect calorimetry. The term "indirect calorimetry" is here defined as a method for calculating heat that living organisms produce from their production of carbon dioxide and nitrogen waste and from their consumption of oxygen, well known to persons skilled in the relevant art.

1. Intravenous Sodium Nitrite and Resting Energy Expenditure

Figure 2:
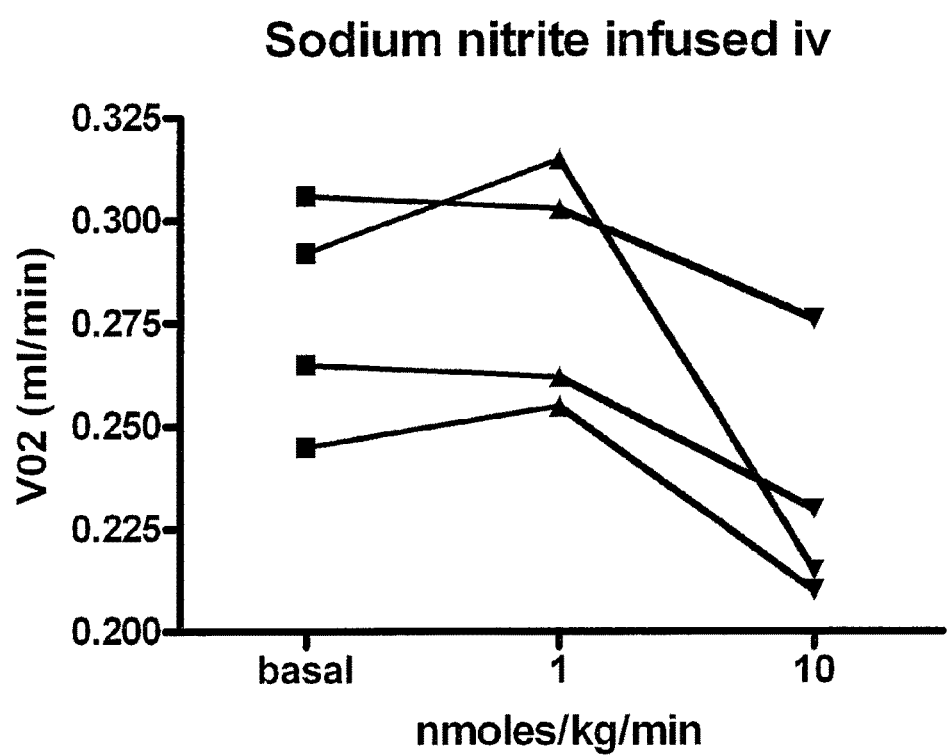
FIG. 2 is a graph showing changes in oxygen consumption ($VO_2$) following iv infusion of sodium nitrite in increasing doses. Nitrite was infused over a 10 min period in non-smoking healthy male volunteers (30-70 years).
Figure 3:
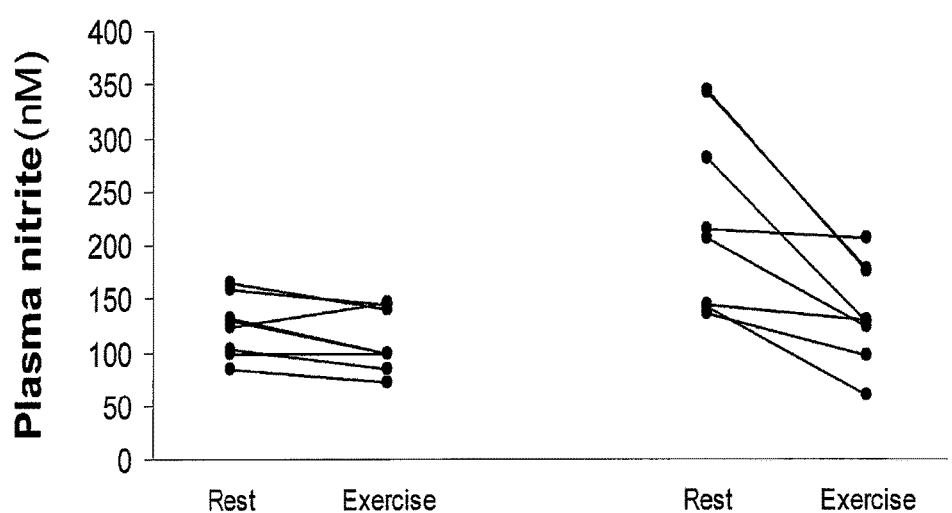
FIG. 3 is a graph showing the effects of a dietary supplementation with sodium nitrate or sodium chloride (placebo) on plasma concentrations of nitrite measured at rest and immediately after exercise in 9 healthy male volunteers.
Figure 4:
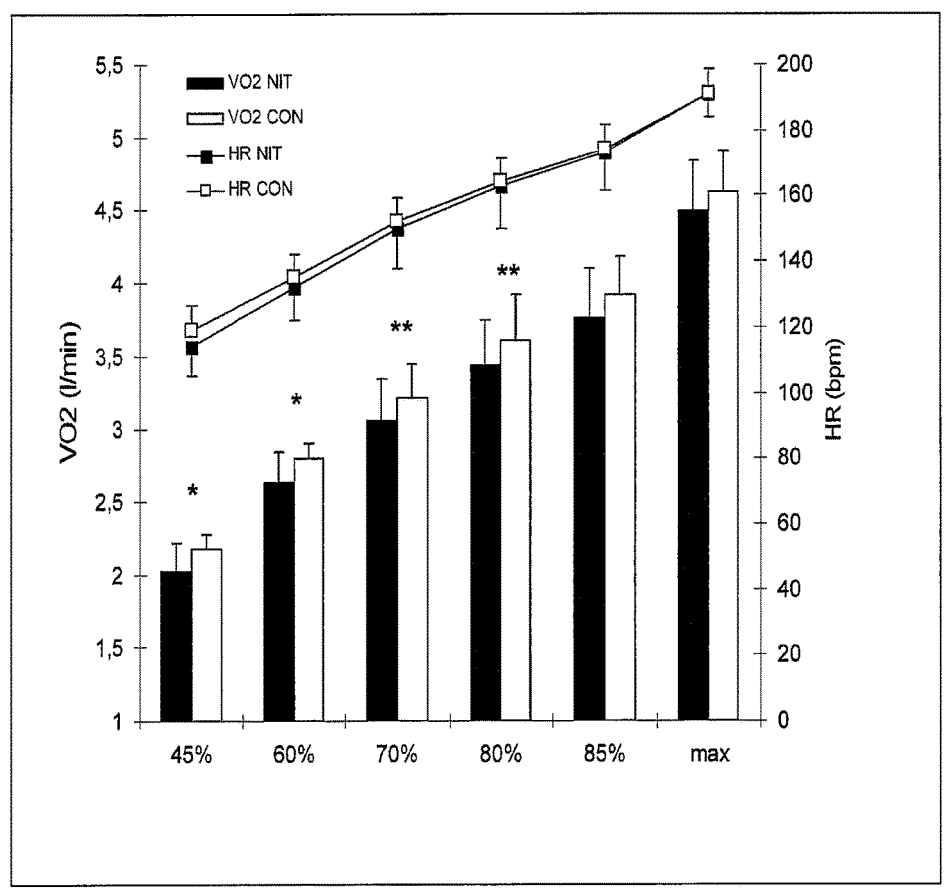
FIG. 4 is a bar diagram showing the oxygen consumption ($VO_2$) and heart rate (HR) measured at 6 different work rates after a 3-day dietary supplementation with sodium nitrate (0.1 mmol/kg/min, NIT) or an equal amount of sodium chloride (CON). The study had a randomized double-blind cross-over design with a washout period of at least 10 days between the tests. *$p<0.05$, **$p<0.01$.

Resting energy expenditure (as measured by indirect calorimetry) is reduced by 10-25% after 10 min of iv infusion of sodium nitrite (n=4, FIG. 3). Prior to the test the subjects had been on a diet low in nitrate for one day and had been fasting for at least 8 h. The major drop in energy expenditure was seen when infusing nitrite at a concentration of 10 nmoles/kg/min during 10 minutes. At 1 nmol/kg/min no obvious effects were noted during the 10 min observation period and after 100 nmol/kg/min no further decrease in oxygen consumption was noted as compared to the 10 nmol dose. In separate experiments (n=2) the present inventors noted an increase in plasma nitrite from 140-165 nM to 370-480 nM after the 10 nmol/kg/min infusion (10 min infusion). Basal levels of methemoglobin were 1.1-1.3 mmol/l and did not change significantly after infusion of nitrite (1.1-1.4 mmol/l) See FIG. 2.

2. Oral Sodium Nitrate and Oxygen Consumption During Exercise

Methods

Subjects: Nine healthy, well-trained ($VO_{2peak}$ 55+/−3.7 ml×kg$^{-1}$×min$^{-1}$), males (28+/−6 years) volunteered for the study. All subjects were trained cyclists or triathletes and well accustomed to the testing procedure. It was chosen to use well-trained subjects to avoid training effects from the tests such as enhanced $VO_{2peak}$ or better mechanical efficiency during submaximal exercise. The protocol was approved by the regional ethics committee in Stockholm and all subjects gave their written consent prior to participation.

Dietary supplementation with nitrate: The aim with the present study was to investigate the effects of two distinct dietary patterns, one with higher, and one with lower than normal nitrate intake. The study had a double-blind placebo-controlled cross-over design. During two three-day periods, separated by a washout interval of ten days, the subjects were instructed to avoid all foods with moderate or high nitrate content (all vegetables, all cured meats, strawberries, grapes, and tea). In addition, they were told to restrain from alcohol and tobacco products. Otherwise they were free to eat any food they liked during the three days of restricted diet. The subjects were randomized to start with either ingestion of 0.1 mmol sodium nitrate/kg bodyweight/day dissolved in water or an equal amount of sodium chloride (placebo). The daily dose was divided and ingested three times daily. The different solutions could not be distinguished by taste or appearance. The daily nitrate dose corresponded to the amount normally found in 150-250 gram of a nitrate-rich vegetable such as spinach, lettuce or beetroot. The last dose of nitrate or placebo was ingested in the morning on the day of measurement (see the main tests below). The order between the nitrate supplementation period (NIT) and the placebo period (CON) was balanced. During the washout period the subjects did not adhere to any specific dietary regime.

Experimental protocol: Measurements were carried out on an electrically braked cycle ergometer (Monark 839E, Varberg, Sweden) that was modified with a racing saddle and the pedal system the subjects were familiar with from training. The bicycle ergometer was computer-controlled, permitting a constant work rate regardless of the cadence the subject chose to pedal with. The pedaling cadence was individually chosen in the range of 70-90 rpm but kept constant during the test to minimize differences in work output due to changes in muscle recruitment patterns.

Pulmonary ventilation ($V_E$), oxygen uptake ($VO_2$), $CO_2$ output ($VCO_2$) and respiratory exchange ratio (RER) were measured at 10 second intervals by a computerised gas analyser (AMIS 2001, Odense, Denmark) connected to a flow meter which the subjects breathed through via a mouthpiece and a plastic tube. Heart rate (HR) was continuously recorded during the tests with a portable heart rate monitor (Polar S610, Polar, Kempele, Finland). Capillary blood samples (20 µl) were collected from the fingertip and were analyzed for lactate ([HIa]) using a Biosen C-Line Sport Analyser (EKF diagnostics, Magdeburg, Germany). Haemoglobin concentration ([Hb]) at rest was determined with capillary blood taken from the fingertip and analyzed with an Hb-measuring device (Hemocue, Ängelholm, Sweden). Hematocrit (Hct) was determined by centrifuging capillary blood at 12000 rpm for three minutes.

Pre-tests: Each subject attended the laboratory twice within a two week period before the first main tests. The first pre-test was carried out to familiarize the subject with the bicycle ergometer and the testing procedure. The subjects did a preliminary test at five submaximal levels with every level lasting for five minutes. There was no rest between the different submaximal levels. $VO_2$ was continuously measured with the AMIS 2001. At the end of each submaximal level capillary blood was taken from the fingertip and later analysed for [HIa]. At every work rate the subjects rated their perceived exertion on the Borg's RPE-scale (BORG, G. Perceived exertion as an indicator of somatic stress. Scand J Rehabil Med. 1970, vol. 2, no. 2, p. 92-8), both central and muscular exertion were rated. After eight minutes of recovery, the subject was instructed to cycle for as long as possible at a work rate corresponding to his calculated maximal oxygen uptake (ÅSTRAND, P-O, et al. Textbook in work physiology. McGraw-Hill, 1970. ISBN 0070024065. p. 619). During this test the subjects actual $VO_{2peak}$ was measured and if the subject was able to cycle for longer than seven minutes extra power of 20-30 watts was added every minute until exhaustion. One and three minutes after the maximal test capillary blood were sampled from the fingertip for analysis of [HIa].

Before the second pre-test, the submaximal levels were adjusted so that they corresponded to 45, 60, 70, 80 and 85% of $VO_{2peak}$. The maximal work rate was also adjusted, if necessary, so that the time to exhaustion was kept between four and seven minutes.

The main tests: The subjects refrained from heavy exercise three days prior to the main tests and avoided all exercise the day before the tests. They were also told to eat their last light meal at least 3 hours before the start of the tests. When the subjects came to the laboratory they received their last dose of either placebo or nitrate and were allowed to rest in the supine position for 60 minutes before the test commenced.

All subjects used a standardised warm up procedure of five min of cycling at 100 watts followed by five minutes of rest. The submaximal and maximal tests were performed in the same way as the second pre-test with five submaximal work rates lasting five minutes each, without rest between the different levels. Identical work rates were used during the two main tests. Venous blood (9 ml) was drawn at rest 45 minutes after the last nitrate/placebo-dose was ingested and again immediately after the $VO_{2peak}$-test. The blood was placed in an ice bath and centrifuged within five minutes at 1300 rpm and 4° C. The plasma was separated and kept at −80° C. until it was analysed for its nitrate and nitrite concentrations by a chemiluminescence assay as described previously (LUNDBERG, J O, et al. Inorganic nitrate is a possible source for systemic generation of nitric oxide. Free Rad Bio Med. 2004, vol. 37, no. 3, p. 395-400).

Statistics and calculations: Results are expressed as means+/−standard deviation (mean+/−SD). Paired t-tests were used to evaluate the difference between the nitrate and the placebo trials. The significance level was set as p=<0.05.

Gross efficiency (GE) was defined as the work rate divided by the actual energy expenditure (EE). The EE was in turn calculated with the Brouwer equation (BROUWER, E. On simple formulae for calculating the heat expenditure and the quantities of carbohydrate and fat oxidized in metabolism of men and animals, from gaseous exchange (Oxygen intake and carbonic acid output) and urine-N. Acta Physiol Pharmacol Neerl. 1957, no. 6, p. 795-802). Delta efficiency (DE) was defined as the increase in work rate divided by the increase in EE (GAESSER, G A, et al. Muscular efficiency during steady-rate exercise: effect of speed and work rate. J Appl Physiol. 1975, no. 38, p.

1132-1139). The DE was based on the four lowest work rates and was analyzed with linear regression. The oxygen pulse is defined as $VO_2/HR$.

Results

Blood pressure at rest: Average resting systolic blood pressure was lower after nitrate supplementation (112+/−8 mmHg) compared to placebo (120+/−5.9, p<0.01). The diastolic blood pressure was also lower after nitrate (68+/−5.5 mmHg) compared to placebo (74+/−6.8 mmHg, p<0.01). Parts of these findings have been published as a separate communication (Larsen et al. 2006).

Blood values: No change was observed in [Hb] at rest (NIT 152+/−11, CON 153+/−11 g×l$^{-1}$, p=0.87) or immediately after the $VO_{2peak}$-test (NIT 163+/−13, CON 161+/−13 g×l$^{-1}$, p=0.27). Nor were there any change in the hematocrit value at rest (NIT 42+/−4, CON 43+/−3%, p=0.19) or after the $VO_{2peak}$-test (NIT 46+/−4, CON 47+/−4%, p=0.6).

Plasma levels of nitrate at rest were 27+/−6.9 μM in CON and 182+/−55 in NIT (p=<0.01). Nitrate levels immediately after the maximal work test were 29+/−6.1 in CON and 175+/−61 μM in NIT (p=<0.01). Plasma nitrate did not change during exercise either in NIT or in CON (p=0.8). Nitrite levels at rest were 124+/−28 in CON and 226+/−87 nM in NIT (p=<0.01). Immediately after the maximal work test the nitrite levels were 111+/−29 in CON and 137+/−48 in NIT (p=0.17).

Figure 6:
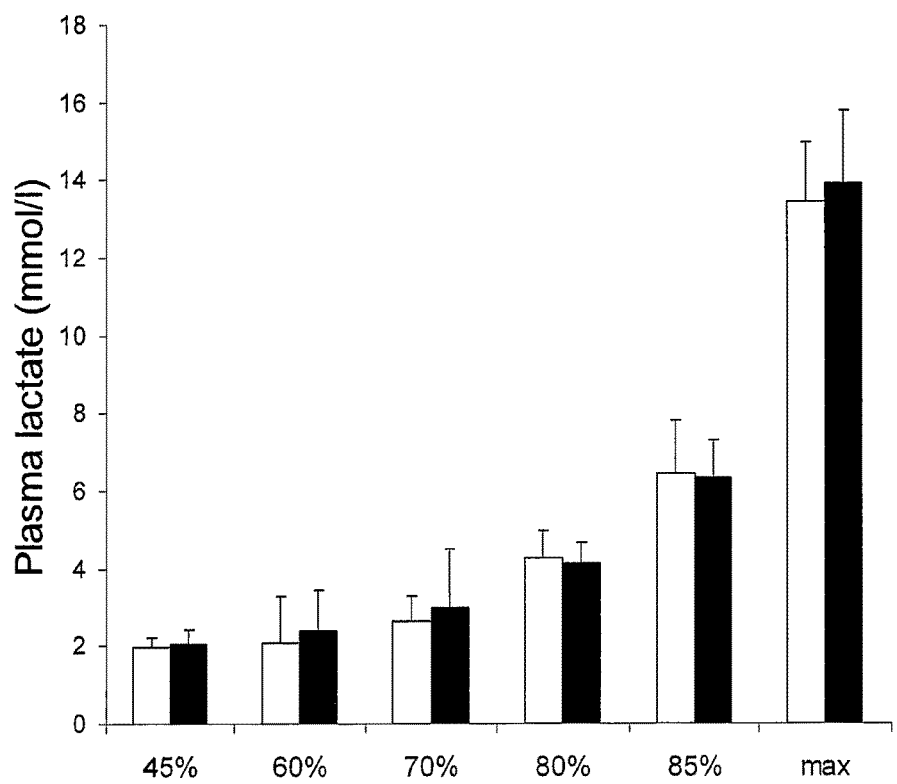
FIG. 6 is a bar diagram showing plasma lactate concentration measured at 6 different work rates after dietary supplementation with sodium nitrate (0.1 mmol/kg/day for 3 days, filled bars) or an equal amount of sodium chloride (placebo, empty bars).

The decrease in nitrite concentrations during exercise was more pronounced in NIT than in CON (FIG. 6). The increase in c-GMP concentrations after the maximal work as compared to rest tended to be higher in NIT than in CON (p=0.08).

Blood pressure: Average resting systolic blood pressure decreased from 120+/−5.9 after NIT to 112+/−8 mmHg after CON (p=0.003). The diastolic blood pressure decreased from 74+/−6.8 to 68+/−5.5 mmHg in the CON and NIT-groups respectively (p=0.005). Parts of these findings have been published as a separate communication (LARSEN, F J, et al. Effects of dietary nitrate on blood pressure in healthy volunteers. N Engl J Med. 2006, vol. 355, no. 26, p. 2792-3).

Figure 5:
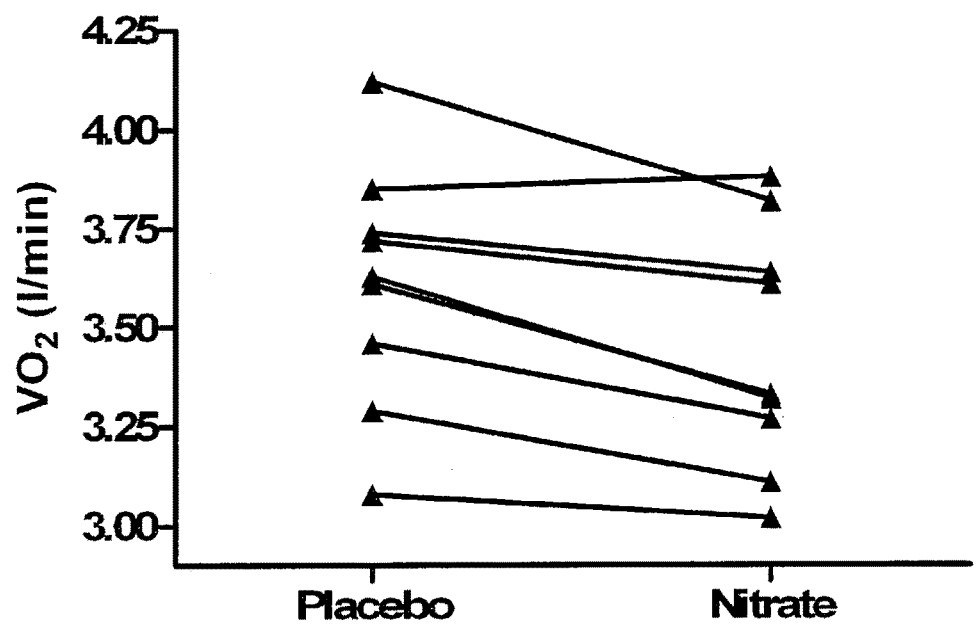
FIG. 5 is a graph showing oxygen consumption during bicycle exercise at 80% of $VO_{2peak}$ in 9 healthy male volunteers. Measurements were made after a 3-day dietary supplementation with sodium nitrate (0.1 mmol/kg/day) or an equal amount of sodium chloride (placebo). The difference between nitrate and placebo periods was significant ($p<0.01$).

Submaximal work parameters: After nitrate administration $VO_2$ was significantly lower during the four work rates corresponding to 45-80% $VO_{2peak}$ compared to the placebo period (FIG. 5). The most significant difference was seen at 80% of $VO_{2peak}$ (NIT 3.44+/−0.31 l×min$^{-1}$ vs CON 3.61+/−0.31 l×min$^{-1}$, p=0.003, FIG. 5). On average $VO_2$ were was 0.15 l×min$^{-1}$ lower in the NIT-trials over the 4 submaximal work rates. There was no difference in heart rate (HR) between the NIT and CON-trials (see FIG. 6). The oxygen pulse tended to decrease from 21.0+/−2.0 during CON to 20.3+/−1.9 ml×beat$^{-1}$ (p=0.08). No significant differences changes were found between NIT and CON in [Hla] (FIG. 6), $V_E$, $V_E/VO2$ or respiratory exchange ratio (RER) during any of the submaximal work rates. The average Gross efficiency (GE) is defined as the work rate divided by the actual energy expenditure (EE). The EE was in turn calculated with the Brouwer equation (Brouwer, supra). GEgross efficiency improved from 19.7% during CON to 21.1% during NIT (p=0.02). Delta efficiency (DE) is the increase in workload divided by the increase in EE (Gaesser & Brooks, supra). The DE is in this case based on the four lowest work rates which were analyzed with a linear regression analysis. The DE Delta efficiency (DE) increased significantly from 22.1+/−1.6% during CON compared to 22.9+/−1.9% during NIT, (p=0.04).

Maximal work capacity: There was no significant difference in the $VO_{2peak}$ between the NIT and CON trials (4.49+/−0.44 and 4.61+/−0.28 l×min$^{-1}$ respectively, p=0.29). These values were also not significantly different from the $VO_{2peak}$ achieved during the pre-test (4.54+/−0.32 l×min$^{-1}$). Likewise, no significant differences were noted either in $V_{Emax}$ (NIT 182+/−21.4 vs CON 186+/−21.7 l×min$^{-1}$, p=0.5), $HR_{max}$ (NIT 189.8+/−7.0 vs CON 190.3+/−7.5 beats×min$^{-1}$, p=0.94) or maximal work rate (NIT 360.6+/−32.8 vs CON 358.9+/−32.3 watt, p=0.35). There was no difference between NIT and CON in the rating of perceived exertion (Borg RPE-scale) at any work load (submax or max).

Comment to the results: In the present study a significantly reduced oxygen demand at submaximal workloads was noted after nitrate administration was noted at the four lowest workloads. The fifth work rate, at approximately 85% $VO_{2peak}$, was well above the lactate threshold in several subjects and thus the anaerobic energy production became more pronounced. This led to involvement of accessory muscle groups and a noticeably change in motion pattern. At this work rate the $VO_2$ did not reach a stable steady-state level and is therefore unsuitable for the calculation of muscular efficiency. The reason for including this fifth work rate in the protocol was to receive a lactate value above the lactate threshold and thereby get an indication of changes in the upper part of the lactate curve.

3. Oral Sodium Nitrate and Glucose Homeostasis

Figure 7A:
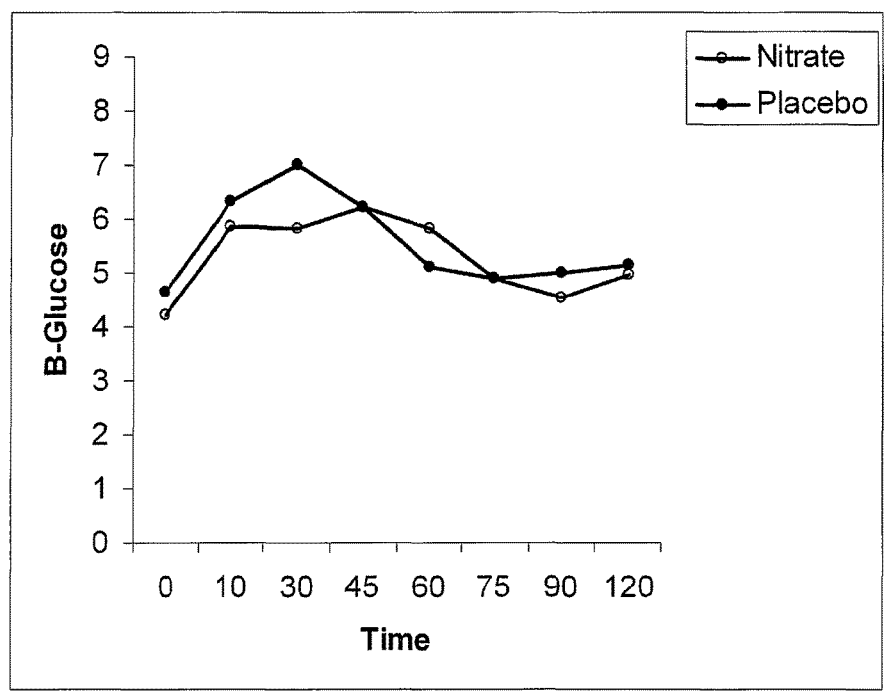
FIG. 7 consists of three graphs, showing changes in blood glucose levels after an oral challenge with glucose for three test subjects in a double-blind, placebo-controlled cross-over study (FIGS. 7a, 7b and 7c). A standard oral glucose tolerance test was performed. The subjects (healthy non-smoking volunteers) had their diet supplemented for 3 days with either sodium chloride (placebo) or sodium nitrate (Nitrate) at a dose of 0.1 mmol/kg/day.
Figure 7B:
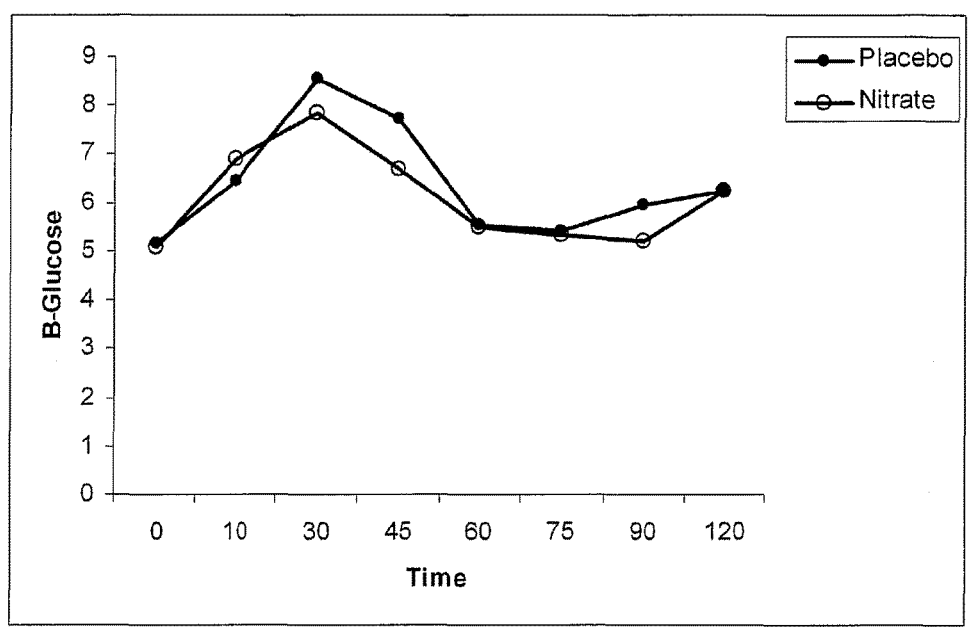
Figure 7C:
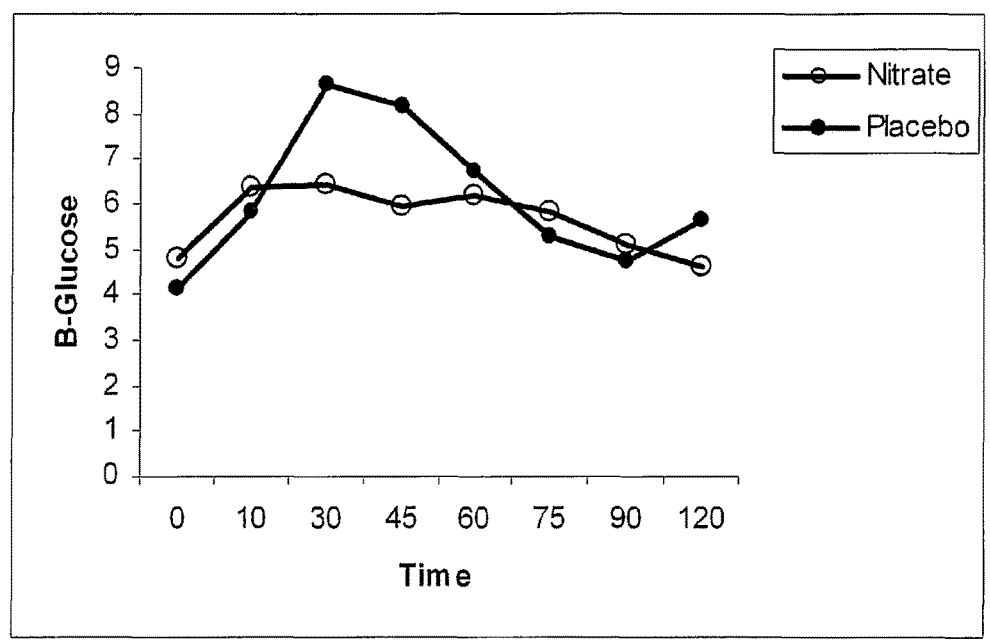

The increase in plasma glucose after a standard Oral Glucose Tolerance Test (75 g glucose in 250 ml water) is lower when measured after nitrate pre-treatment (1 mmol/kg NaNO$_3$) compared to placebo (NaCl). The study was performed with three healthy test subjects in a double-blind study. Glucose ingestion started 60 min after the nitrate ingestion. Blood glucose levels were measured during the 120 min period after the glucose load (n=3). At 30 min mean plasma glucose was 8.2 mmol/l with placebo and in the same subjects 6.5 mmol/l after nitrate supplementation. The results are shown in FIGS. 7a, b, and c.

Figure 8:
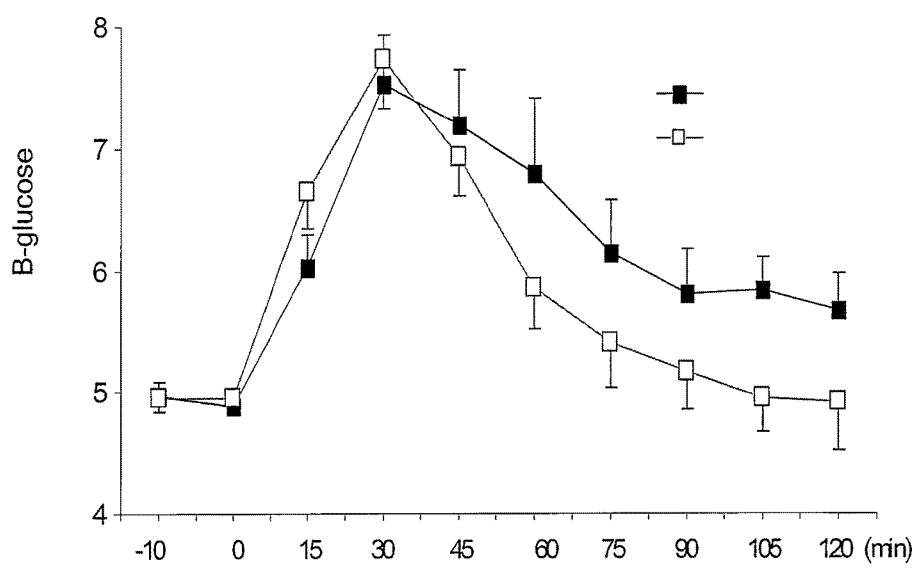
FIG. 8 is a graph showing changes in blood glucose levels after an oral challenge with glucose in 8 additional subjects in a double-blind, placebo-controlled cross-over study. A standard oral glucose tolerance test was performed. The subjects (healthy non-smoking volunteers) had their diet supplemented for 3 days with either sodium chloride (PLACEBO) or sodium nitrate (NITRATE) at a dose of 0.1 mmol/kg/day. Data are presented as mean±SEM.

The lower increase in plasma glucose after nitrate pre-treatment was verified in a further study wherein a standard Oral Glucos Tolerance Test (75 g glucose) was performed in 8 healthy non-smoking subjects after a three-day supplementation with either sodium chloride or sodium nitrate at equal molar amounts (0.1 mmol/kg/day). The study had a double-blind, placebo-controlled, cross-over design. Blood glucose levels were measured at two time points before (−10 and 0 min) and at 15, 30, 45, 60, 75, 90, 105 and 120 min after glucose intake (n=8). At the occasion when the subjects had taken nitrate, the area under the curve for blood glucose was smaller compared to when they had ingested placebo. The results are shown in FIG. 8 as mean±SEM.

4. Effect of Ingestion of Beetroot on Blood Pressure

A 43 year old non-smoking subject with hypertension ingested fresh beetroot juice (300-400 ml/day) for 14 days. The blood pressure was measured twice a day for 14 days and then twice on day 20 (counted from day 1 of treatment). The Basal blood pressure was 142/99 on the day when the experiment started.

Figure 9:
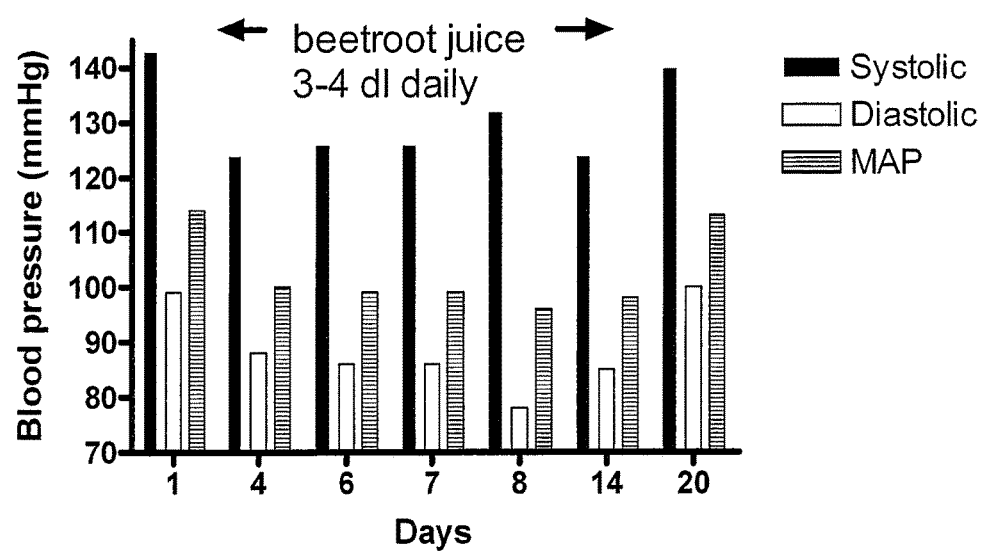
FIG. 9 is a graph showing the effect of a two-week intervention with beetroot juice (fresh juice 3-4 dl/day) on systolic, diastolic and mean arterial (MAP) blood pressure in a 43 year old male with hypertension.

The results from the ingestion of beetroot juice are shown in FIG. 9. The mean of the two daily measurements are shown in the bars. With ingestion of the beetroot juice (between day 1-14) a mean reduction in systolic pressure of ≈15 mmHg and a mean reduction in diastolic pressure of ≈16 mmHg was seen. When measured again 6 days after stopping beetroot juice treatment (day 20), the blood pressure had increased to basal levels (140/100). Pulse rate was unchanged throughout the experimental period. MAP=mean arterial pressure.

5. Concentrations of Plasma Nitrite after Intravenous Infusion of Nitrate

Methods

Anesthetised rats (n=11) were given a bolus dose (10 mg/kg body weight) of $NaNO_3$ (open boxes) and blood samples were collected at indicated time points. 7 additional rats were pre-treated with 30 mg/kg body weight of allopurinol given intra peritoneally 60 minutes prior to the $NaNO_3$ infusion (closed triangles) and blood samples were collected at the time points indicated. Allopurinol inhibits the xanthionoxidase, an enzyme suggested being involved in the reduction of nitrate to nitrite in mammal cells. Plasma was extracted and analysed for nitrate and nitrite.

Three different strains of mice—wild type (n=5 placebo, n=5 nitrate), germ free (n=5 placebo, n=5 nitrate) and eNOS knockout mice (n=2 placebo, n=3 nitrate), were given an intra peritoneal injection of 10 mg/kg nitrate or placebo (NaCl) and plasma level of nitrite measured 1 hour later.

Results

Figure 10:
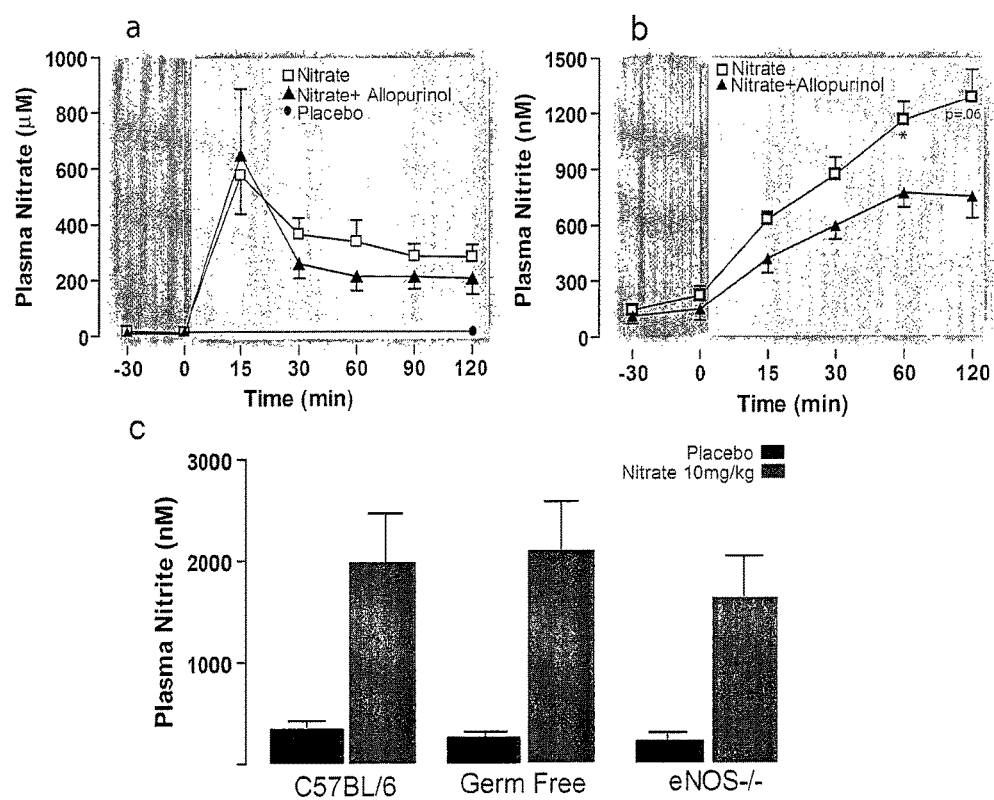
FIG. 10 shows the plasma nitrate and nitrite concentrations after intravenous infusion of nitrate. a) shows plasma nitrate concentrations, b) shows plasma nitrite concentrations and c) shows plasma nitrite concentrations in wild type (C57BL/6), germ free and knockout (eNOS) mice.

The results from the intravenous infusion of nitrate are shown in FIG. 10 a-c. FIG. 10a shows the plasma nitrate concentration and FIG. 10b shows the plasma nitrite concentration. After infusion of nitrate the concentration of plasma nitrate increases dramatically both in rats that received nitrate and rats that received nitrate+allopurinol (a). The plasma nitrite concentrations increased in rats that received nitrate as well as in rats that received nitrate+allopurinol, (b). However the increase in the rats that received only nitrate was significantly greater, *p<0.05.

FIG. 10c shows that nitrate-induced increase in plasma nitrite is equal in wild type (n=5 placebo, n=5 nitrate), germ free (n=5 placebo, n=5 nitrate) and eNOS knockout mice (n=2 placebo, n=3 nitrate), p=0.05*.

Previously it has been suggested that only bacterial cells and not mammalian cells can reduce nitrate to nitrite. These results surprisingly show that also mammalian cells can metabolise nitrate to nitrite. Further, they suggest that the xanthionoxidase enzyme is involved in the reduction of nitrate to nitrite.

6. Enhancement of Post-Ischemic Blood Flow

Rats received an intravenous bolus dose of 10 mg/kg nitrate ($NaNO_3$, n=4) or placebo (NaCl, n=4)) diluted in PBS (pH 7.4) followed by continuous infusion of 3 mg/kg/h. 60 minutes after the addition of nitrate (open boxes) or placebo (filled circles), L-NAME (50 mg/kg) was given and 10 minutes later a supra renal clamping of the abdominal aorta was performed. After 30 minutes of ischemia the clamp was removed and the abdominal aortic blood flow was monitored during 60 minutes.

Figure 11:
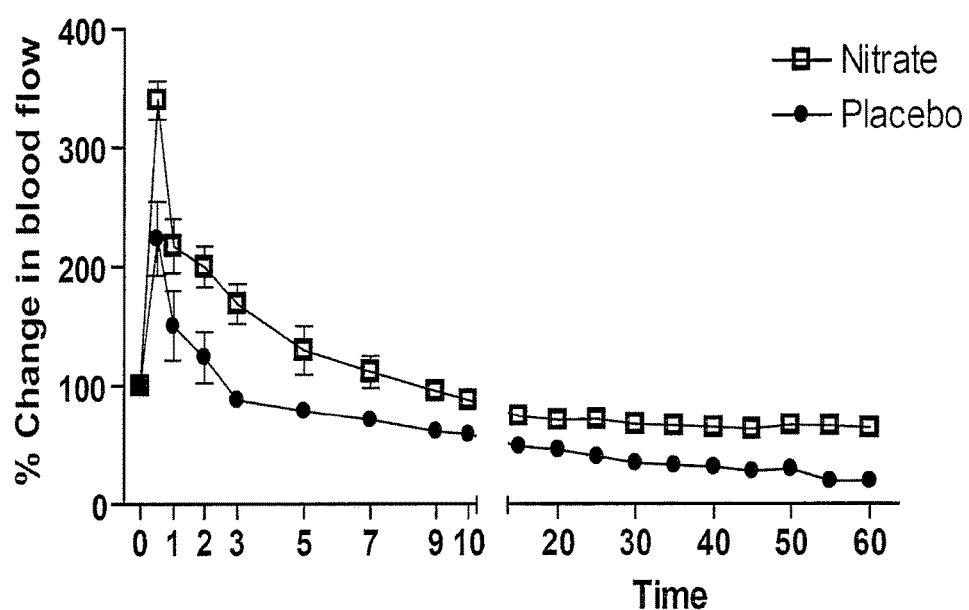
FIG. 11 is a graph showing enhanced post-ischemic blood flow after nitrate infusion.

The results show that the nitrate-treated rats maintain a higher blood flow during the early (0-10 minutes) as well as the late (10-60 minutes) post-ischemic phase compared to the placebo treated rats (FIG. 11). Remarkably, after 60 min of reperfusion the blood flow had decreased to only 20% of pre-ischemic values in the control rats, while in the nitrate-treated rats, the blood flow was maintained at almost 75% of control values. This demonstrates a strong augmentation of the nitrate-nitrite-NO pathway during an ischemic event.

Although the invention has been described with regard to its preferred embodiments, which constitute the best mode presently known to the inventors, it should be understood that various changes and modifications as would be obvious to one having the ordinary skill in this art may be made without departing from the scope of the invention as set forth in the claims appended hereto.

REFERENCES

WO 2005/004884 A (US GOVERNMENT ET AL.) 20 Jan. 2005

WO 2005/007173 A (US GOVERNMENT ET AL.) 27 Jan. 2005

Joint FAO/WHOExpert Committee on Food Additives (JECFA). Safety Evaluation of Certain Food Additives. WHO, 1970. ISBN 9241660503.

TANNENBAUM, S. R., et al. Nitrite in human saliva. Its possible relationship to nitrosamine formation. J cancer Ins. 1974, vol. 53, p. 79-84.

BARTSCH, H., et al. Inhibitors of endogenous nitrosation: mechanisms and implications in human cancer prevention. Mutation Res. 1988, vol. 202, p. 307-324.

LUNDBERG, Jon O., et al. Nitrate, bacteria and human health. Nat Rev Microbiol. 2004, no. 2, p. 593-602.

MODIN, A., et al. Nitrite-derived nitric oxide: a possible mediator of 'acidic-metabolic' vasodilation. Acta Physiol Scand. 2001, vol. 171, p. 9-16.

COSBY, K., et al. Nitrite reduction to nitric oxide by deoxyhemoglobin vasodilates the human circulation. Nat Med. 2003, no. 9, p. 1498-505.

SPIEGELHALDER, B., et al. Influence of dietary nitrate on nitrite content of human saliva: possible relevance to in vivo formation of N-nitroso compounds. Food Cosmet Toxicol. 1976, no. 14, p. 545-548.

LUNDBERG, Jon O., et al. Inorganic nitrate is a possible source for systemic generation of nitric oxide. Free Radic Biol Med. 2004, vol. 37, p. 395-400.

DURANSKI, M. R., et al. Cytoprotective effects of nitrite during in vivo ischemia-reperfusion of the heart and liver. J Clin Invest. 2005, vol. 115, p. 1232-1240.

GLADWIN, M. T., et al. The emerging biology of the nitrite anion. Nat Chem Biol. 2005, no. 1, p. 308-14.

LARSEN, F. J., et al. Effects of dietary nitrate on blood pressure in healthy volunteers. N Engl J Med. 2006, vol. 355, p. 2792-3.

BORG, G. Perceived exertion as an indicator of somatic stress. Scand J Rehabil Med. 1970, vol. 2, no. 2, p. 92-8.

ÅSTRAND, P-O, et al. Textbook in work physiology. McGraw-Hill, 1970. ISBN 0070024065. p. 619.

LUNDBERG, J O, et al. Inorganic nitrate is a possible source for systemic generation of nitric oxide. Free Rad Bio Med. 2004, vol. 37, no. 3, p. 395-400.

BROUWER, E. On simple formulae for calculating the heat expenditure and the quantities of carbohydrate and fat oxidized in metabolism of men and animals, from gaseous exchange (Oxygen intake and carbonic acid output) and urine-N. Acta Physiol Pharmacol Neerl. 1957, no. 6, p. 795-802.

GAESSER, G A, et al. Muscular efficiency during steady-rate exercise: effect of speed and work rate. J Appl Physiol. 1975, no. 38, p. 1132-1139.

LARSEN, F J, et al. Effects of dietary nitrate on blood pressure in healthy volunteers. N Engl J Med. 2006, vol. 355, no. 26, p. 2792-3.

The invention claimed is:

1. A method for decreasing whole body oxygen consumption in a human subject with metabolic stress caused by a condition selected from the group consisting of: surgery, malnutrition, cancer, burn injury, traumatic injury, anorexia nervosa, thyroid disorder, stress ulcer, sleep apnea, septic shock, insufficient perfusion of the intestines, and disturbed glucose homeostasis, the method consisting of:

orally administering to said human subject an anion of nitrate ($NO_3^-$) in an effective amount that provides nitrate ($NO_3^-$) in a dose of 0.01-1 mmole/kg body weight/24 h and in a form selected from the group consisting of: a liquid, chewing gum, tablet, lozenge, wafer, cake, and bar, wherein the administration results in decreased whole body oxygen consumption in said human subject.

2. A method for decreasing whole body oxygen consumption in a human subject with metabolic stress caused by a condition selected from the group consisting of: surgery, malnutrition, cancer, burn injury, traumatic injury, anorexia nervosa, thyroid disorder, stress ulcer, sleep apnea, septic shock, insufficient perfusion of the intestines, and disturbed glucose homeostasis, the method comprising orally administering to said human subject a composition comprising two physiologically active pharmaceuticals, wherein one physiologically active pharmaceutical is an anion of nitrate ($NO_3^-$) and the other physiologically active pharmaceutical is an anion of nitrite ($NO_2^-$), wherein the anion of nitrate ($NO_3^-$) is from at least one plant and is in an effective amount that provides nitrate ($NO_3^-$) in a dose of 0.01-1 mmole/kg body weight/24 h and the ratio of nitrate ($NO_3^-$) to nitrite ($NO_2^-$) is about 5:1 to about 100:1 and wherein the administration results in decreased whole body oxygen consumption in said human subject.

3. The method according to claim 2, wherein the ratio of nitrate ($NO_3^-$) to nitrite ($NO_2^-$) is about 5:1 to 30:1.

4. The method according to claim 1, wherein the salt of nitrate ($NO_3^-$) is isolated from one or more nitrate-rich vegetables and/or fruits.

5. The method according to claim 2, wherein the ratio of nitrate ($NO_3^-$) to nitrite ($NO_2^-$) is about 10:1.

6. The method according to claim 1, wherein the salt of nitrate ($NO_3^-$) is administered in the form of a lozenge.

7. The method according to claim 1, wherein the anion of nitrate is a sodium, potassium, calcium, zinc, arginine, or ammonium salt.

8. The method according to claim 2, wherein the anion of nitrite ($NO_2^-$) is a sodium, potassium, calcium, zinc, arginine, or ammonium salt.

9. A method for decreasing whole body oxygen consumption in a human subject with metabolic stress caused by a condition selected from the group consisting of: surgery, malnutrition, cancer, burn injury, traumatic injury, anorexia nervosa, thyroid disorder, stress ulcer, sleep apnea, septic shock, insufficient perfusion of the intestines, and disturbed glucose homeostasis, the method consisting of orally administering to said human subject a composition consisting of:

an anion of nitrate ($NO_3^-$) in an effective amount that provides nitrate ($NO_3^-$) in a dose of 0.01-1 mmole/kg body weight/24 h;

non-pathogenic live bacteria selected from the group consisting of: probiotic bacteria, *Veillonella* species, *Staphylococcus* species, *Actinomyces* species, and *Rothia* species, and at least one carrier, wherein the anion of nitrate ($NO_3^-$) is from at least one plant and wherein the composition reacts locally in the gastrointestinal tract via bacteria-dependent reduction of nitrate to NO and other bioactive nitrogen oxides and the administration of the composition results in decreased whole body oxygen consumption in said human subject.

10. A method for decreasing whole body oxygen consumption in a human subject with metabolic stress caused by a condition selected from the group consisting of: surgery, malnutrition, cancer, burn injury, traumatic injury, anorexia nervosa, thyroid disorder, stress ulcer, sleep apnea, septic shock, insufficient perfusion of the intestines, and disturbed glucose homeostasis, the method consisting of orally administering to said human subject a composition consisting of:

an anion of nitrate ($NO_3^-$) in an effective amount that provides nitrate ($NO_3^-$) in a dose of 0.01-1 mmole/kg body weight/24 h, and a polyphenol-rich compound or product, wherein the anion of nitrate ($NO_3^-$) is from at least one plant and the administration of the composition results in decreased whole body oxygen consumption in said human subject.

11. A method for decreasing whole body oxygen consumption in a human subject with metabolic stress caused by a condition selected from the group consisting of: surgery, malnutrition, cancer, burn injury, traumatic injury, anorexia nervosa, thyroid disorder, stress ulcer, sleep apnea, septic shock, insufficient perfusion of the intestines, and disturbed glucose homeostasis, the method comprising:

administering to said human subject a composition comprising one physiologically active pharmaceutical, wherein the physiologically active pharmaceutical is a nitrite ($NO_2^-$), wherein the nitrite ($NO_2^-$) is administered orally or intravenously in an effective amount that provides nitrite ($NO_2^-$) in a dose of 0.01-100 µmole/kg body weight and the administration results in decreased whole body oxygen consumption in said human subject.

12. The method of claim 1, wherein the disturbed glucose homeostasis is a condition selected from the group consisting of: diabetes mellitus type 1, diabetes mellitus type 2, drug-induced diabetes, metabolic syndrome, and obesity.

13. The method of claim 11, wherein the disturbed glucose homeostasis is a condition selected from the group consisting of: diabetes mellitus type 1, diabetes mellitus type 2, drug-induced diabetes, metabolic syndrome, and obesity.

14. The method according to claim 2, wherein the composition further comprises ascorbic acid.

15. The method according to claim 2, wherein the composition has the form of a liquid, chewing gum, tablet, lozenge, wafer, cake, or bar.

16. The method according to claim 2, wherein the composition has the form of a lozenge.

17. The method according to claim 2, wherein the anion of nitrate is a sodium, potassium, calcium, zinc, arginine, or ammonium salt.

18. The method according to claim 2, wherein the composition further comprises non-pathogenic live bacteria and reacts locally in the gastrointestinal tract via bacteria-dependent reduction of nitrate and nitrite to NO and other bioactive nitrogen oxides, wherein the non-pathogenic live bacteria are selected from the group consisting of: probiotic bacteria, *Veillonella* species, *Staphylococcus* species, *Actinomyces* species, and *Rothia* species.

* * * * *

UNITED STATES PATENT AND TRADEMARK OFFICE
CERTIFICATE OF CORRECTION

| | |
|---|---|
| PATENT NO. | : 10,406,118 B2 |
| APPLICATION NO. | : 12/528794 |
| DATED | : September 10, 2019 |
| INVENTOR(S) | : Jon Lundberg and Eddie Weitzberg |

Page 1 of 1

It is certified that error appears in the above-identified patent and that said Letters Patent is hereby corrected as shown below:

In the Claims

Column 23 Line 30 reads "salt" should read - anion -

Column 23 Line 35 reads "salt" should read - anion -

Signed and Sealed this
Twenty-seventh Day of October, 2020

Andrei Iancu
*Director of the United States Patent and Trademark Office*